US009175390B2

(12) United States Patent
Pore et al.

(10) Patent No.: US 9,175,390 B2
(45) Date of Patent: Nov. 3, 2015

(54) SYNTHESIS AND USE OF PRECURSORS FOR ALD OF TELLURIUM AND SELENIUM THIN FILMS

(75) Inventors: Viljami Pore, Helsinki (FI); Timo Hatanpää, Espoo (FI); Mikko Ritala, Espoo (FI); Markku Leskelä, Espoo (FI)

(73) Assignee: ASM International N.V. (NL)

( * ) Notice: Subject to any disclaimer, the term of this patent is extended or adjusted under 35 U.S.C. 154(b) by 139 days.

(21) Appl. No.: 12/429,133

(22) Filed: Apr. 23, 2009

(65) Prior Publication Data

US 2010/0009078 A1 Jan. 14, 2010

Related U.S. Application Data

(60) Provisional application No. 61/048,077, filed on Apr. 25, 2008, provisional application No. 61/112,128, filed on Nov. 6, 2008, provisional application No. 61/117,896, filed on Nov. 25, 2008.

(51) Int. Cl.
    *C23C 16/00* (2006.01)
    *C23C 16/455* (2006.01)
    *C23C 16/30* (2006.01)
    (Continued)

(52) U.S. Cl.
    CPC ......... *C23C 16/45553* (2013.01); *C23C 16/306* (2013.01); *H01L 45/06* (2013.01); *H01L 45/1233* (2013.01); *H01L 45/143* (2013.01); *H01L 45/144* (2013.01);
    (Continued)

(58) Field of Classification Search
    USPC ............... 427/248.1, 255.28, 255.29, 255.31
    See application file for complete search history.

(56) References Cited

U.S. PATENT DOCUMENTS

| 6,706,115 B2 | 3/2004 | Leskela et al. |
| 6,716,713 B2 | 4/2004 | Todd |

(Continued)

FOREIGN PATENT DOCUMENTS

| EP | 1 995 236 | 11/2008 |
| JP | 04-226930 | 8/1992 |

(Continued)

OTHER PUBLICATIONS

Bhasin et al., "Synthesis of Alkali Metal TellurideS and Ditellurides in THF and their Relative Reactivities Toward Alkyl Bromides: A Convenient Synthesis of Dialkyl Tellurides and Dialkyl Ditellurides," Indian Journal of Chemistry, Jul. 1991, vol. 30A, pp. 632-634.

(Continued)

*Primary Examiner* — David Turocy
(74) *Attorney, Agent, or Firm* — Knobbe, Martens Olson & Bear LLP

(57) ABSTRACT

Atomic layer deposition (ALD) processes for forming Te-containing thin films, such as Sb—Te, Ge—Te, Ge—Sb—Te, Bi—Te, and Zn—Te thin films are provided. ALD processes are also provided for forming Se-containing thin films, such as Sb—Se, Ge—Se, Ge—Sb—Se, Bi—Se, and Zn—Se thin films are also provided. Te and Se precursors of the formula $(Te,Se)(SiR^1R^2R^3)_2$ are preferably used, wherein $R^1$, $R^2$, and $R^3$ are alkyl groups. Methods are also provided for synthesizing these Te and Se precursors. Methods are also provided for using the Te and Se thin films in phase change memory devices.

42 Claims, 29 Drawing Sheets

(51) Int. Cl.
*H01L 45/00* (2006.01)
*H01L 21/02* (2006.01)

(52) U.S. Cl.
CPC ........ *H01L 45/1616* (2013.01); *H01L 21/0256* (2013.01); *H01L 21/0262* (2013.01); *H01L 21/02562* (2013.01)

(56) References Cited

U.S. PATENT DOCUMENTS

| | | | |
|---|---|---|---|
| 7,482,286 | B2 | 1/2009 | Misra et al. |
| 7,817,464 | B2 | 10/2010 | Kuh et al. |
| 2006/0180811 | A1* | 8/2006 | Lee et al. ........................ 257/40 |
| 2007/0048977 | A1 | 3/2007 | Lee et al. |
| 2007/0054475 | A1* | 3/2007 | Lee et al. ...................... 438/483 |
| 2007/0249086 | A1* | 10/2007 | Philipp et al. ................... 438/95 |
| 2008/0017841 | A1 | 1/2008 | Lee et al. |
| 2008/0026578 | A1 | 1/2008 | Shenai-Khatkhate et al. |
| 2008/0093591 | A1 | 4/2008 | Khang et al. |
| 2008/0096386 | A1 | 4/2008 | Park et al. |
| 2008/0108175 | A1 | 5/2008 | Shin et al. |
| 2009/0074652 | A1* | 3/2009 | Dussarrat ...................... 423/508 |
| 2009/0112009 | A1 | 4/2009 | Chen et al. |
| 2009/0124039 | A1 | 5/2009 | Roeder et al. |
| 2009/0137100 | A1* | 5/2009 | Xiao et al. .................... 438/478 |
| 2009/0191330 | A1 | 7/2009 | Xiao |
| 2009/0280052 | A1 | 11/2009 | Xiao et al. |
| 2009/0305458 | A1* | 12/2009 | Hunks et al. .................. 438/102 |
| 2010/0317150 | A1 | 12/2010 | Hunks et al. |

FOREIGN PATENT DOCUMENTS

| | | |
|---|---|---|
| JP | 2002-322181 | 11/2002 |
| JP | 2007-186784 | 7/2007 |
| JP | 2009-149980 | 7/2009 |
| JP | 2009-535369 | 5/2010 |
| JP | 2010-514918 | 5/2010 |
| KR | 10-2006-0091160 | 8/2006 |
| KR | 2007-0066114 | 6/2007 |
| KR | 2008-0035864 | 4/2008 |
| WO | WO 2007/133837 | 11/2007 |
| WO | WO 2008/057616 | 5/2008 |
| WO | WO 2009/132207 | 10/2009 |

OTHER PUBLICATIONS

Choi et al., "Combined Atomic Layer and Chemical Vapor Deposition, and Selective Growth of $Ge_2Sb_2Te_5$ Films on TiN/W Contact Plug," Chem. Mater., 2007, vol. 19, pp. 4387-4389.
Chong et al., "Phase Change Random Access Memory Cell with Superlattice-like Structure," Applied Physics Letters, 2006, vol. 88, pp. 122114-1 to 122114-3.
Detty et al., "Bis(trialkylsilyl) Chalcogenides. 1. Preparation and Reduction of Group 6A Oxides," J. Org. Chem., 1982, vol. 47, pp. 1354-1356.
Evans et al. "Synthesis and use of tris(trimethylsilyl)antimony for the preparation of InSb Quantum Dots" Chemistry of Materials, vol. 20, No. 18, 2008, pp. 5727-5730.
Groshens et al., "Low Temperature MOCVD Growth of V/VI Materials Via a $Me_3SiNMe_2$ Elimination Reaction," 15th International Conference on Thermoelectrics, 1996, pp. 430-434.
Groshens et al., "Room-Termperature MOCVD of $Sb_2Te_3$ Films and Solution Precipitation of $M_2Te_3$ (M=Sb, Bi) Powders via a Novel (*N*,*N*-Dimethylamino)trimethylsilane Elimination Reaction," Chem. Mater., 1994, vol. 6, pp. 727-729.
Jang et al., "Structural Stability and Phase-Change Characteristics of $Ge_2Sb_2Te_5/SiO_2$ Nano-Multilayered Films," Electrochemical and Solid-State Letters, 2009, vol. 12, Issue 4, pp. H151-H154.
Lacaita, "Phase change memories: State-of-the-art, challenges and perspectives," Solid-State Electronics, 2006, vol. 50, pp. 24-31.
Lee et al., "GeSbTe Deposition for the PRAM Application," Applied Surface Science, 2007, vol. 253, pp. 3969-3976.

W.L. Lehn, "Preparation of tris(trimethylsilyl)-and tris(trimethylstannyl)amines" Communications to the Editor, Jan. 1964, p. 305.
Pore, "Atomic Layer Deposition of Metal Tellurides and Selenides Using Alkylsilyl Compounds of Tellurium and Selenium," J. Am. Chem. Soc., 2009.
Ritala et al., "Atomic Layer Deposition of $Ge_2Sb_2Te_5$ Thin Films," Microelectronic Engineering, 2009.
Singh, "Organotellurium Precursors for Metal Organic Chemical Vapour Deposition (MOCVD) of Mercury Cadmium Telluride (MCT)," Polyhedron, Mar. 1996, vol. 15, Issue 5-6, pp. 745-763.
Singh, "Recent Developments in the Ligan Chemistry of Tellurium," Coordination Chemistry Reviews, Nov. 2000, vol. 209, Issue 1, pp. 49-98.
Sisido et al. "Formation of an Organotin-nitroen bond. Syntheses of tris(trialkyltin)amines" Apr. 1964, vol. 29, pp. 907-909.
Wells et al. "Use of tris(trirnethylsily)arsine to prepare gallium arsenide and indium arsenide", Chemistry of Materials 1989, vol. 1, pp. 4-6.
Wuttig et al., "Phase-Change Materials for Rewriteable Data Storage," Nature Materials, Nov. 2007, vol. 6, pp. 824-832.
Supplemental European Search Report for EP 09735227 dated Mar. 3, 2011 (7 pages).
Malik et al. "Gallium arsenide nanoparticles-synthesis and characterisation" J. Mater. Chem, 2003 vol. 13, pp. 2591-2595.
Viljami Pore et al. "Atomic layer deposition of metal tellurides and selenides using alkylsilyl compounds of tellurium" J. Am. Chem. Soc. 2009, vol. 131 pp. 3478-3480.
Evans et al. "Synthesis and use of tris(trimethylsilyl)antimony for the preparation of InSb quantum dots" Chem. Mater. 2008, vol. 20, No. 18, pp. 5727-5730.
International Search Report for PCT/US2010/053982 dated Jun. 28, 2011.
English translation of Chinese Office Action, issued Jan. 23, 2013 in Chinese Patent Application No. 200980124332.8.
Downs, A., "Chemistry of Aluminum, Gallium, Indium and Thallium", London: Chapman & Hall 1 993, p. 188.
Herzog, U., "New chalcogen derivatives of silicon possessing adamantine and noradamantane structures", Journal of Organometallic Chemistry, 2001, vol. 628, pp. 133-143.
Office Action in Chinese Application No. 200980124332.8, filed Apr. 23, 2009, dated Mar. 29, 2012.
Office Action dated Oct. 21, 2014 in Japanese Application No. 2011-506454 with English Translation.
Sewing, D. et al.; "Diacyltellurides: Synthesis by Reactions of Acyl Chlorides with Bis(trialkylsilyl)tellurides. Structure Determinations of Di(1-adamantoyl)telluride and Adamantanecarbonic Anhydride," Zeitschrift fuer Anorganische und Allgemeine Chemie, 1998, vol. 624, pp. 1363-1368.
English Translation of Japanese Office Action issued in Japanese Application No. 2011-506454, dated Sep. 17, 2013.
Lee et al., "*Influences of metal, non-metal precursors, and substrates on atomic layer deposition processes for the growth of selected functional electronic materials*", Coord. Chem. Rev., 2013, 23 pages.
V. Pore, "*ALD of phase change materials Ge2Sb2Te5*", ASM Meeting, Sep. 10, 2007, University of Helsinki.
V. Pore, "*ALD of Sb2Te3, GeTe and Ge2Sb2Te5-phase change materials*", ASM Meeting, May 15, 2008, University of Helsinki.
M. Ritala, *Atomic Layer Deposition of phase change materials*, 11th E\PCOS (European\Phase Change and Ovonics Symposium) 2012 Proceedings, Jul. 8-10, 2012 Tampere, Finland, downloaded http://www.epcos.org/library/papers/pdf_2012/Oral-Papers/S3-03.pdf, Mar. 17, 2015.
Bochkarev et al. "Reaction of triethylsilanethiol and related compounds with triethylaluminum", Bulletin of the Academy of Sciences of the USSR Division of Chemical Science, Sep. 1, 1971, pp. 1881-1884.

(56) References Cited

OTHER PUBLICATIONS

Drake et al., "Studies of silyl and germyl Group VI species. Part IV. Dimetyl-and tetramethyl-disilyl chalcogenides and related species", Can. J. Chem., vol. 58, No. 58, Jan. 1, 1980, pp. 2161-2166.

Extended European Search Report dated Feb. 25, 2015 in Application No. 15150242.4.

Herzog et al., "Dimeric and trimeric diorganosilicon chalcogenides (PhRSiE) 2,3 (E=S, Se, Te; R=Ph, Me)", Journal of Organometallic Chemistry, vol. 689, No. 26, Dec. 20, 2004, pp. 4909-4916.

Schultz et al., "Selenium and Tellurium Chalcogenides as Mild and Efficient Reducing Agents for Alpha-Halo Ketones", Synthesis, No. 8, Aug. 1, 1998, pp. 11-37-1140.

Singh et al., "Organotellurium Precursors for Metal Organic Chemical Vapour Deposition (MOCVD) of Mercury Cadmium Telluride (MCT)", Polyhedron, vol. 15, No. 5-6, Mar. 1, 1996, pp. 745-763.

Notice of Allowance dated Feb. 24, 2015 in Japanese Application No. 2011-506454.

\* cited by examiner

SYNTHESIS AND USE OF PRECURSORS FOR ALD OF TELLURIUM AND SELENIUM THIN FILMS

REFERENCE TO RELATED APPLICATIONS

The present application claims priority under 35 U.S.C. §119(e) to U.S. Provisional Application No. 61/048,077 filed Apr. 25, 2008; Ser. No. 61/112,128 filed Nov. 6, 2008; and Ser. No. 61/117,896 filed Nov. 25, 2008; entitled SYNTHESIS AND USE OF PRECURSORS FOR ALD OF TELLURIUM AND SELENIUM THIN FILMS, which are all hereby incorporated by reference in their entirety.

PARTIES OF JOINT RESEARCH AGREEMENT

The invention claimed herein was made by, or on behalf of, and/or in connection with a joint research agreement between the University of Helsinki and ASM Microchemistry signed on Nov. 14, 2003. The agreement was in effect on and before the date the claimed invention was made, and the claimed invention was made as a result of activities undertaken within the scope of the agreement.

BACKGROUND OF THE INVENTION

1. Field of the Invention

The present application relates generally to methods and compounds for forming thin films comprising tellurium (Te) or selenium (Se) by atomic layer deposition. Such films may find use, for example, in phase change memory (PCM) devices and in optical storage media.

2. Description of the Related Art

Thin films comprising Te and Se are used in many different applications, including, for example, non-volatile phase-change memories (PCM), solar cells, and optical storage materials. The operation of PCM cells is based on the resistivity difference between amorphous and crystalline states of the active material. A resistivity difference of more than three orders of magnitude can be obtained by many different phase change alloys. The switching in a PCM cell is generally accomplished by heating the material locally with suitable current pulses, which, depending on the intensity of the pulse, leave the material in a crystalline or amorphous state.

A wide variety of different PCM cell structures have been reported, many of which use trench or pore-like structures. Sputtering has typically been used in preparing PCM materials, but the more demanding cell structures will require better conformality and more control of the deposition process. Sputtering may be capable of forming simple pore and trench structures, however, future PCM applications will require more complicated 3-D cell structures that cannot be formed using sputtering techniques. Processes with greater precision and control, such as atomic layer deposition (ALD), will be required to make these complicated structures. Using an atomic layer deposition process provides greater precision and control over the deposition, including better conformality and better control of the composition of the deposited film.

Atomic layer deposition processes for depositing Te and Se-containing thin films have been limited, in part, by a lack of appropriate precursors.

A need exists, therefore, for methods for controllably and reliably forming thin films of phase change materials comprising tellurium and selenium by ALD.

SUMMARY OF THE INVENTION

The methods disclosed herein provide reliable atomic layer deposition (ALD) methods for forming thin films comprising tellurium and for making precursors that can be used in such methods.

In accordance with one aspect of the present invention, atomic layer deposition processes for forming a Te or Se containing thin film are provided. In some embodiments, the processes include a plurality of deposition cycles. In some embodiments, each deposition cycle comprises: providing a pulse of a first vapor phase reactant into the reaction chamber to form no more than about a single molecular layer of the first reactant on the substrate; removing excess first reactant from the reaction chamber; providing a pulse of a second vapor phase Te or Se reactant to the reaction chamber such that the second vapor phase reactant reacts with the first reactant on the substrate to form Te or Se containing thin film, wherein the Te or Se reactant is $Te(SiR^1R^2R^3)_2$ or $Se(SiR^1R^2R^3)_2$, wherein $R^1$, $R^2$, and $R^3$ are alkyl groups with one or more carbon atoms; and removing excess second reactant and reaction byproducts, if any, from the reaction chamber.

In accordance with another aspect of the present invention, ALD processes for forming a Sb containing thin film on a substrate in a reaction chamber are provided. The processes comprise a plurality of deposition cycles, each cycle comprising: providing a pulse of a first vapor phase Sb reactant into the reaction chamber to form no more than about a single molecular layer of the Sb reactant on the substrate, wherein the Sb reactant comprises $SbX_3$, wherein X is a halogen; removing excess first reactant from the reaction chamber; providing a pulse of a second vapor phase reactant to the reaction chamber such that the second vapor phase reactant reacts with the Sb reactant on the substrate to form a Sb containing thin film; and removing excess second reactant and reaction byproducts, if any, from the reaction chamber.

In accordance with another aspect of the present invention, ALD processes for forming a Ge containing thin film on a substrate in a reaction chamber are provided. The processes comprising: providing a first vapor phase reactant pulse comprising a Ge precursor into the reaction chamber to form no more than about a single molecular layer of the Ge precursor on the substrate, wherein the Ge precursor has a formula of $GeX_2$, wherein X are halides (F, Cl, Br or I); removing excess first reactant from the reaction chamber; providing a second vapor phase reactant pulse to the reaction chamber such that the second vapor phase reactant reacts with the Ge precursor on the substrate; removing excess second reactant and reaction byproducts, if any, from the reaction chamber; and repeating the providing and removing steps until a film of a desired thickness is formed.

In accordance with another aspect of the present invention, ALD processes for forming a Te or Se containing thin film are provided. The processes comprising: alternately and sequentially contacting a substrate with a vapor phase reactant pulse comprising a first precursor and a vapor phase reactant pulse comprising a second precursor comprising Te or Se, wherein the second precursor comprises Te or Se bound to two Si atoms; and repeating the alternate and sequential pulses until a thin film of a desired thickness is obtained.

In accordance with another aspect of the present invention, processes for making a Te or Se precursor are provided. The processes comprising: forming a first product by reacting a Group IA metal with a material comprising Te or Se; and subsequently adding a second reactant comprising a silicon atom bound to a halogen atom, thereby forming a compound comprising Te or Se bound to two silicon atoms.

DETAILED DESCRIPTION OF THE PREFERRED EMBODIMENT

Figure 1:
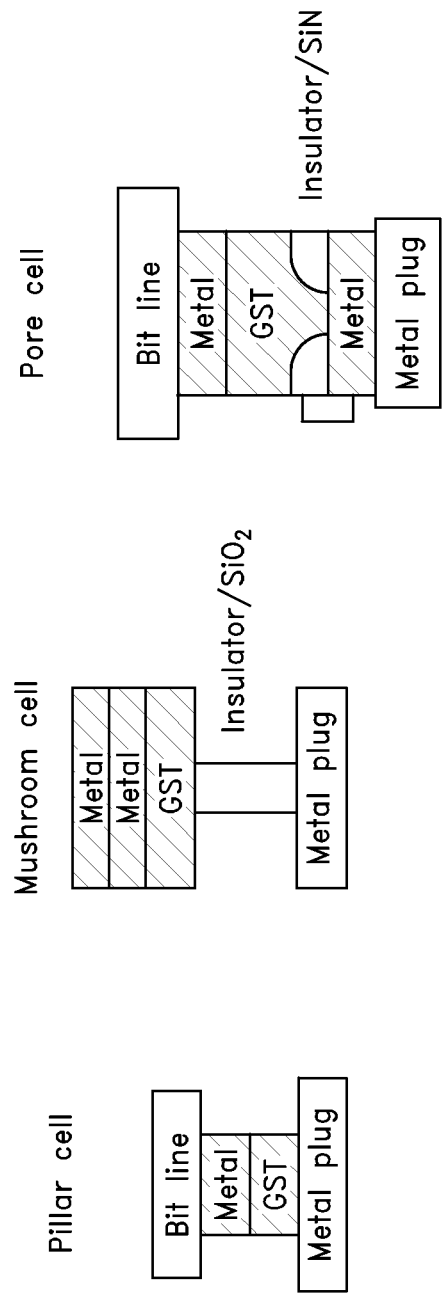
FIG. 1 illustrates schematic cross sections of various types of PCM structures.

As discussed above, Te and Se-containing films find use in a variety of applications, including phase change memory (PCM), solar cells, and optical storage materials. PCM cells can have a variety of different configurations. Typically, the PCM cell includes a transistor and a resistor between a top metal contact and a resistive bottom electrode. Additional PCM configurations are disclosed, for example, in "Phase change memories: State-of-the-art, challenges and perspectives" by Lacaita, Solid-State Electronics 50 (2006) 24-31, which is herein incorporated by reference in its entirety. FIG. 1 illustrates three schematic cross sections of configurations of PCM cells, including a pillar cell, mushroom cell, and pore cell.

Solar cell absorber materials can comprise a variety of different materials. Some of the most promising solar cell absorber materials are $CuInSe_2$-based chalcopyrite materials. $CuSe_x$ also can be used in solar cells.

While the embodiments of the present invention are discussed in the general context of PCM, the skilled artisan will appreciate that the principles and advantages taught herein will have application to other devices and applications. Furthermore, while a number of processes are disclosed herein, one of ordinary skill in the art will recognize the utility of certain of the disclosed steps in the processes, even in the absence of some of the other disclosed steps, and similarly that subsequent, prior and intervening steps can be added.

Antimony-telluride (including Sb—Te and $Sb_2Te_3$), Germanium-telluride (including GeTe), germanium-antimony-telluride (GST; $Ge_2Sb_2Te_5$), bismuth-telluride BiTe (including $Bi_2Te_3$), and zinc-telluride (including ZnTe) thin films can be deposited on a substrate by atomic layer deposition (ALD) type processes. ALD type processes are based on controlled, self-limiting surface reactions of precursor chemicals. Gas phase reactions are avoided by feeding the precursors alternately and sequentially into the reaction chamber. Vapor phase reactants are separated from each other in the reaction chamber, for example, by removing excess reactants and/or reactant byproducts from the reaction chamber between reactant pulses.

Tellurium has several oxidation states, including −2, 0, +2, +4, and +6. Antimony has several oxidation states, including −3, +3, 0 and +5, of which +3 is most common. A stoichiometric Sb—Te film with Te in a −2 oxidation state comprises $Sb_2Te_3$. Germanium (Ge) has oxidation states of 0, +2, and +4.

Tellurium (Te) compounds, where Te has an oxidation state of −2, are generally called tellurides. Tellurium compounds, where Te has an oxidation state of 0, are generally called tellurium compounds. However, for the sake of simplicity, as used herein thin films comprising Te are referred to as tellurides. Thus films referred to as tellurides herein may contain Te with oxidations states other than −2, for example, oxidation states of 0, +2, +4, and +6. It will be apparent to the skilled artisan when a particular oxidation state is intended.

Briefly, a substrate is loaded into a reaction chamber and is heated to a suitable deposition temperature, generally at lowered pressure. Deposition temperatures are maintained below the thermal decomposition temperature of the reactants but at a high enough level to avoid condensation of reactants and to provide the activation energy for the desired surface reactions. Of course, the appropriate temperature window for any given ALD reaction will depend upon the surface termination and reactant species involved. Here, the temperature varies depending on the type of film being deposited and is preferably at or below about 400° C., more preferably at or below about 200° C. and most preferably from about 20° C. to about 200° C.

A first reactant is conducted or pulsed into the chamber in the form of a vapor phase pulse and contacted with the surface of the substrate. Conditions are preferably selected such that no more than about one monolayer of the first reactant is adsorbed on the substrate surface in a self-limiting manner. The appropriate pulsing times can be readily determined by the skilled artisan based on the particular circumstances. Excess first reactant and reaction byproducts, if any, are removed from the reaction chamber, such as by purging with an inert gas.

Purging the reaction chamber means that vapor phase precursors and/or vapor phase byproducts are removed from the reaction chamber such as by evacuating the chamber with a vacuum pump and/or by replacing the gas inside the reactor with an inert gas such as argon or nitrogen. Typical purging times are from about 0.05 to 20 seconds, more preferably between about 1 and 10, and still more preferably between about 1 and 2 seconds. However, other purge times can be utilized if necessary, such as where highly conformal step coverage over extremely high aspect ratio structures or other structures with complex surface morphology is needed.

A second gaseous reactant is pulsed into the chamber where it reacts with the first reactant bound to the surface. Excess second reactant and gaseous byproducts of the surface reaction, if any, are removed from the reaction chamber, preferably by purging with the aid of an inert gas and/or evacuation. The steps of pulsing and purging are repeated until a thin film of the desired thickness has been formed on the substrate, with each cycle leaving no more than a molecular monolayer. Additional phases comprising provision of a reactant and purging of the reaction space can be included to form more complicated materials, such as ternary materials.

As mentioned above, each pulse or phase of each cycle is preferably self-limiting. An excess of reactant precursors is supplied in each phase to saturate the susceptible structure surfaces. Surface saturation ensures reactant occupation of all available reactive sites (subject, for example, to physical size or "steric hindrance" restraints) and thus ensures excellent step coverage.

Removing excess reactants can include evacuating some of the contents of the reaction space and/or purging the reaction space with helium, nitrogen or another inert gas. In some embodiments purging can comprise turning off the flow of the reactive gas while continuing to flow an inert carrier gas to the reaction space.

The precursors employed in the ALD type processes may be solid, liquid or gaseous materials under standard conditions (room temperature and atmospheric pressure), provided that the precursors are in vapor phase before they are conducted into the reaction chamber and contacted with the substrate surface. "Pulsing" a vaporized precursor onto the substrate means that the precursor vapor is conducted into the chamber for a limited period of time. Typically, the pulsing time is from about 0.05 to 10 seconds. However, depending on the substrate type and its surface area, the pulsing time may be even higher than 10 seconds. Pulsing times can be on the order of minutes in some cases. The optimum pulsing time can be determined by the skilled artisan based on the particular circumstances.

The mass flow rate of the precursors can also be determined by the skilled artisan. In some embodiments the flow rate of metal precursors is preferably between about 1 and 1000 sccm without limitation, more preferably between about 100 and 500 sccm.

The pressure in the reaction chamber is typically from about 0.01 to about 20 mbar, more preferably from about 1 to about 10 mbar. However, in some cases the pressure will be higher or lower than this range, as can be determined by the skilled artisan given the particular circumstances.

Before starting the deposition of the film, the substrate is typically heated to a suitable growth temperature. The growth temperature varies depending on the type of thin film formed, physical properties of the precursors, etc. The growth temperatures are discussed in greater detail below in reference to each type of thin film formed. The growth temperature can be less than the crystallization temperature for the deposited materials such that an amorphous thin film is formed or it can be above the crystallization temperature such that a crystalline thin film is formed. The preferred deposition temperature may vary depending on a number of factors such as, and without limitation, the reactant precursors, the pressure, flow rate, the arrangement of the reactor, crystallization temperature of the deposited thin film, and the composition of the substrate including the nature of the material to be deposited on. The specific growth temperature may be selected by the skilled artisan.

Examples of suitable reactors that may be used include commercially available ALD equipment such as the F-120® reactor, Pulsar® reactor and Advance® 400 Series reactor, available from ASM America, Inc of Phoenix, Ariz. and ASM Europe B.V., Almere, Netherlands. In addition to these ALD reactors, many other kinds of reactors capable of ALD growth of thin films, including CVD reactors equipped with appropriate equipment and means for pulsing the precursors can be employed. Preferably, reactants are kept separate until reaching the reaction chamber, such that shared lines for the precursors are minimized. However, other arrangements are possible, such as the use of a pre-reaction chamber as described in U.S. application Ser. No. 10/929,348, filed Aug. 30, 2004 and Ser. No. 09/836,674, filed Apr. 16, 2001, the disclosures of which are incorporated herein by reference.

The growth processes can optionally be carried out in a reactor or reaction space connected to a cluster tool. In a cluster tool, because each reaction space is dedicated to one type of process, the temperature of the reaction space in each module can be kept constant, which improves the throughput compared to a reactor in which is the substrate is heated up to the process temperature before each run.

A stand-alone reactor can be equipped with a load-lock. In that case, it is not necessary to cool down the reaction space between each run.

The following examples illustrate certain preferred embodiments of the invention. They were carried out in an F-120™ ALD reactor supplied by ASM Microchemistry Oy, Espoo.

Te and Se Precursors for Atomic Layer Deposition

Any of the following precursors can be used in the various ALD processes disclosed herein. In particular, precursors comprising Te and Se are disclosed.

In some embodiments the Te or Se precursor has Te or Se bound to two silicon atoms. For example it can have a general formula of $A(SiR^1R^2R^3)_2$, wherein A is Te or Se and $R^1$, $R^2$, and $R^3$ are alkyl groups comprising one or more carbon atoms. The $R^1$, $R^2$, and $R^3$ alkyl groups can be selected independently of each other in each ligand based on the desired physical properties of the precursor such as volatility, vapor pressure, toxicity, etc. In some embodiments, $R^1$, $R^2$ and/or $R^3$ can be hydrogen, alkenyl, alkynyl or aryl groups. In some embodiments, $R^1$, $R^2$, $R^3$ can be any organic groups containing heteroatoms, such as N, O, F, Si, P, S, Cl, Br or I. In some embodiments $R^1$, $R^2$, $R^3$ can be halogen atoms. In some embodiments the Te precursor is $Te(SiMe_2{}^tBu)_2$ and the Se precursor is $Se(SiMe_2{}^tBu)_2$. In other embodiments the precursor is $Te(SiEt_3)_2$, $Te(SiMe_3)_2$, $Se(SiEt_3)_2$ or $Se(SiMe_3)_2$. In more preferred embodiments the precursor has a Te—Si or Se—Si bond and most preferably Si—Te—Si or Si—Se—Si bond structure.

In some embodiments the Te or Se precursor has a general formula of $[R^1R^2R^3X^1]_3$—Si-A-Si—$[X^2R^4R^5R^6]_3$, wherein A is Te or Se; and wherein $R^1$, $R^2$, $R^3$, $R^4$, $R^5$ and $R^6$, can be independently selected to be alkyl, hydrogen, alkenyl, alkynyl or aryl groups. In some embodiments, $R^1$, $R^2$, $R^3$, $R^4$, $R^5$ and $R^6$ can be any organic groups containing also heteroatoms, such as N, O, F, Si, P, S, Cl, Br or I. In some embodiments $R^1$, $R^2$, $R^3$, $R^4$, $R^5$ and $R^6$ can be halogen atoms. In some embodiments $X^1$ and $X^2$ can be Si, N, or O. In some embodiments $X^1$ and $X^2$ are different elements. In embodiments when X is Si then Si will be bound to three R groups, for example $[R^1R^2R^3Si]_3$—Si-A-Si—$[SiR^4R^5R^6]_3$. In embodiments when X is N then nitrogen will only be bound to two R groups ($[R^1R^2N]_3$—Si-A-Si—$[NR^3R^4]_3$). In embodiments when X is O, the oxygen will only be bound to one R group, for example $[R^1$—$O]_3$—Si-A-Si—$[O$—$R^2]_3$. $R^1$, $R^2$, $R^3$, $R^4$, $R^5$ and $R^6$ groups can be selected independently of each other in each ligand based on the desired physical properties of the precursor such as volatility, vapor pressure, toxicity, etc In some embodiments the Te or Se precursors is selected from the group consisting of: $R^1R^2R^3Si$—Si-A-Si—$SiR^4R^5R^6$; $R^1R^2N$—Si-A-Si—$NR^3R^4$; $R^1$—O—Si-A-Si—O—$R^2$; or $R^1R^2Si$-A-$SiR^3R^4$ with a double bond between silicon and one of the R groups. In other embodiments the Te or Se precursor comprises: a ring or cyclical configuration comprising a Te or Se atom and multiple Si atoms; or comprises more than one Te atoms or more than one Se atoms. In these embodiments A is Te or Se and $R^1$, $R^2$, $R^3$, $R^4$, $R^5$ and $R^6$, are selected from the group consisting of alkyl, hydrogen, alkenyl, alkynyl, or aryl groups. In some embodiments the Te or Se precursor is not $A(SiR^1R^2R^3)_2$.

In some embodiments the Te or Se precursor has a formula similar to the formulas described above, however the Si atom has a double bond to one of the R groups in the ligand (e.g. A—Si=) wherein A is Te or Se. For example, a partial structure of the precursor formula is represented below:

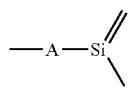

In some embodiments the precursor contains multiple atoms of Si and Te or Se. For example, a partial structure of a precursor in one embodiment is represented below wherein A is Te or Se:

The Si atoms in the partial formula pictured above can also be bound to one or more R groups. In some embodiments, any of the R groups described herein can be used.

In some embodiments the precursor contains a Si—Te—Si or Si—Se—Si bond structure in a cyclical or ring structure. For example, a partial structure of a precursor in one embodiment is represented below, wherein A is Te or Se.

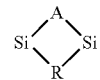

The R group can comprise an alkyl, alkenyl, alkynyl, alkylsilyl, alkylamine or alkoxide group. In some embodiments the R group is substituted or branched. In some embodiments the R group is not substituted and/or is not branched. The Si atoms in the partial formula pictured above can also be bound to one or more R groups. In some embodiments, any of the R groups described herein can be used.

Metal Precursors for ALD in Combination With Te or Se Precursors of the Present Invention Any of the following metal precursors can be used in the various ALD processes disclosed herein. Some metal precursors that can be used in combination with the Te and Se precursors disclosed herein. In particular metal precursors in which metal is bonded to nitrogen, oxygen or carbon and that have ability to form a bond with silicon are preferred.

In some embodiments the metal precursor is metal-organic or organometallic precursor. In some embodiments the metal precursor is a halide precursor. In some embodiments the metal precursor has an adduct forming ligand.

Preferred precursors include, but are not limited to metal halides, alkyls, alkoxides, amides, silylamides, amidinates, cyclopentadienyls, carboxylates, β-diketonates and β-diketoimines.

Preferred metals in metal precursors include, but are not limited to Sb, Ge, Bi, Zn, Cu, In, Ag, Au, Pb, Cd, Hg, More preferred Sb precursors include, Sb halides, such as $SbCl_3$, $SbBr_3$ and $SbI_3$, Sb alkoxides, such as $Sb(OEt)_3$ and Sb amides.

More preferred Ge precursors include Ge halides, such as $GeCl_2$ and $GeBr_2$, adducted derivatives of $GeCl_2$ and $GeBr_2$, such as $GeCl_2$-dioxane, More preferred Bi precursors include Bi halides, such as $BiCl_3$.

More preferred Zn precursors include elemental Zn, Zn halides, such as $ZnCl_2$, and alkyl zinc compounds such $Zn(Et)_2$ or $Zn(Me)_2$.

More preferred Cu compounds, include Cu carboxylates, such as Cu(II)-pivalate, Cu halides, such as CuCl and $CuCl_2$, Cu β-diketonates, such as $Cu(acac)_2$ or $Cu(thd)_2$ and Cu-amidinates.

More preferred In compounds, include In halides, such as $InCl_3$ and In alkyl compounds, such as $In(CH_3)_3$.

More preferred Pb compounds include Pb alkyls, such as tetraphenyl lead $Ph_4Pb$ or tetraethyl lead $Et_4Pb$.

Pulsing Order for Te and Se Compounds in ALD Cycles

The pulsing order for reactants in an ALD cycle can be chosen by the skilled artisan. Preferably the Te or Se compound precursor pulse is after the metal precursor pulse and purge in the deposition cycle. However, different pulsing schemes for Te and Se compounds can be used. In some embodiments the Te or Se compound is pulsed as a second precursor. In some embodiments the Te or Se compound is pulsed as a first precursor. A skilled artisan can determine the appropriate pulsing schemes for deposition of films comprising three or more elements, such as Ge—Sb—Te.

Atomic Layer Deposition of Sb—Te

In some embodiments, $Sb_xTe_y$, preferably $Sb_2Te_3$, films are deposited by ALD preferably without the use of plasma; however in some cases plasma might be used, if needed. For example, if elemental Te films or Te-rich films are desired, plasma, such as hydrogen plasma, hydrogen radicals or atomic hydrogen, may be used. Another use for plasma is doping of the films, for example doping by O, N or Si may be done using plasma. Reliable methods for forming Sb—Te thin films by ALD without hydrogen plasma are not previously known in the art. Finding suitable Te and Sb precursors compatible with ALD processes has been challenging as many precursors do not result in film growth or are extremely toxic. Hydride reactants $H_2Te$ and $H_2Se$ are highly toxic gases and thus are difficult to work with. Other reactants containing hydrogen-Te and hydrogen-Se bonds are also believed to be extremely toxic. For example, it is know that the toxicity of arsenic based compounds increases as the number of hydrogen-As bonds increases. It is likely that the toxicity of Te and Se compounds also increases as the number of hydrogen-Te and hydrogen-Se bonds increases. The alkyl derivatives $R_2Te$ and $R_2Se$ are less toxic and less volatile; however, they are not as reactive. Some of the compounds described herein may have some level of toxicity. However, it is preferable to use precursors with lower toxicity with sufficient reactivity, when feasible.

Figure 2:
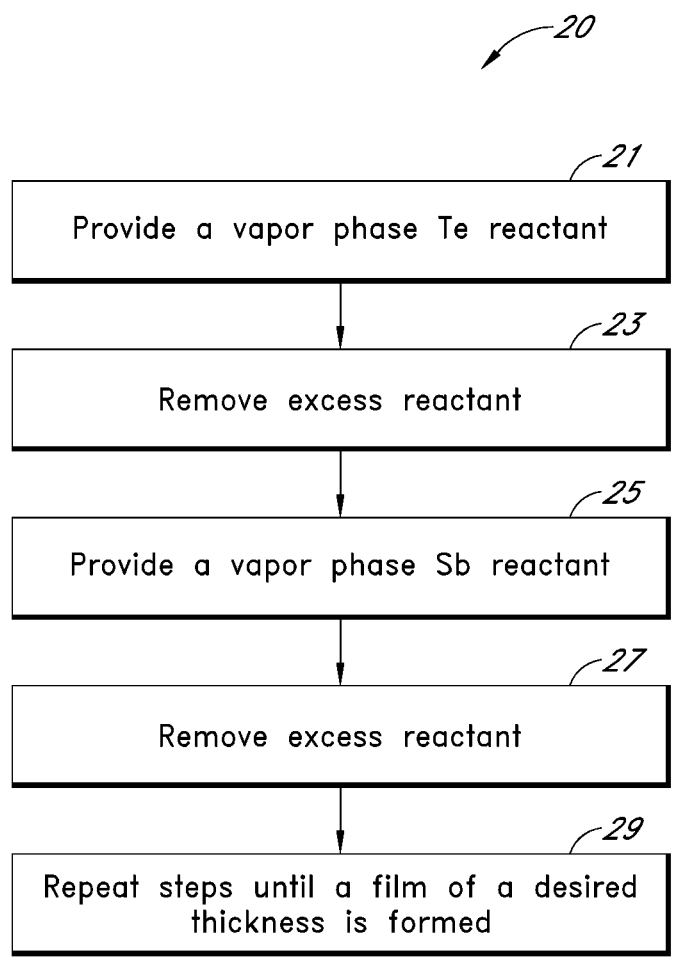
FIG. 2 is a flow chart generally illustrating a method for forming a Sb—Te film in accordance with one embodiment.

FIG. 2 is a flow chart generally illustrating a method for forming a Sb—Te thin film 20 in accordance with one embodiment. According to some embodiments, an $Sb_2Te_3$ thin film is formed on a substrate in a reaction chamber by an ALD type process comprising multiple Sb—Te deposition cycles, each deposition cycle comprising:

- providing a first vapor phase reactant pulse comprising a Te precursor 21 into the reaction chamber to form no more than about a single molecular layer of the Te precursor on the substrate;
- removing excess first reactant from the reaction chamber 23;
- providing a second vapor phase reactant pulse comprising an Sb precursor 25 to the reaction chamber such that the Sb precursor reacts with the Te precursor on the substrate to form $Sb_2Te_3$; and
- removing excess second reactant and reaction byproducts, if any, from the reaction chamber 27.

This can be referred to as the Sb—Te deposition cycle. Each Sb—Te deposition cycle typically forms at most about one monolayer of $Sb_2Te_3$. The Sb—Te deposition cycle is repeated until a film of a desired thickness is formed 29. In some embodiments an Sb—Te film of from about 10 Å to about 2000 Å, preferably from about 50 Å to about 500 Å is formed.

Although the illustrated Sb—Te deposition cycle begins with provision of the Te precursor, in other embodiments the deposition cycle begins with the provision of the Sb precursor.

In some embodiments, the reactants and reaction by-products can be removed from the reaction chamber by stopping the flow of Te or Sb precursor while continuing the flow of an inert carrier gas such as nitrogen or argon.

Preferably, the Te precursor has a formula of $Te(SiR^1R^2R^3)_2$, wherein $R^1$, $R^2$, and $R^3$ are alkyl groups comprising one or more carbon atoms. The $R^1$, $R^2$, and $R^3$ alkyl groups can be selected on the desired physical properties of the precursor such as volatility, vapor pressure, toxicity, etc. In some embodiments the Te precursor is $Te(SiMe_2{}^tBu)_2$. In other embodiments the precursor is $Te(SiEt_3)_2$ or $Te(SiMe_3)_2$.

In some embodiments the Sb source is $SbX_3$, wherein X is a halogen element. More preferably the Sb source is $SbCl_3$ or $SbI_3$.

In some embodiments the Te precursor is $Te(SiEt_3)_2$ and the Sb precursor is $SbCl_3$.

The substrate temperature during forming the Sb—Te thin film is preferably less than 250° C. and more preferably less than 200° C. and even more preferably below 100° C. If an amorphous thin film is desired the temperature can be lowered even further down to at or below about 90° C. In some embodiments the deposition temperature can be below about 80° C., below about 70° C., or even below about 60° C.

Pressure of the reactor can vary much depending from the reactor used for the depositions. Typically reactor pressures are below normal ambient pressure.

The skilled artisan can determine the optimal reactant evaporation temperatures based on the properties of the selected precursors. The evaporation temperatures for the Te precursor, such as $Te(SiMe_2{}^tBu)_2$ and $Te(SiEt_3)_2$, which can be synthesized by the methods described herein, is typically about 40° C. to 45° C. $Te(SiMe_3)_2$ has a slightly higher vapor pressure than $Te(SiMe_2{}^tBu)_2$ or $Te(SiEt_3)_2$ and thus $Te(SiMe_3)_2$ evaporation temperature is slightly lower from about 20 to 30° C. The evaporation temperature for the Sb precursor, such as $SbCl_3$, is typically about 30° C. to 35° C.

The skilled artisan can determine the optimal reactant pulse times through routine experimentation based on the properties of the selected precursors and the desired properties of the deposited Sb—Te thin film. Preferably the Te and Sb reactants are pulsed for about 0.05 to 10 seconds, more preferably about 0.2 to 4 seconds, and most preferably about 1 to 2 seconds. The purge steps in which excess reactant and reaction by-products, if any, are removed are preferably about 0.05 to 10 seconds, more preferably about 0.2-4 seconds, and most preferably 1 to 2 seconds in length.

The growth rate of the Sb—Te thin films will vary depending on the reaction conditions. As described below, in initial experiments, the growth rate varied between about 0.019 and 0.025 Å/cycle for higher reaction temperatures. Higher growth rates were observed at lower temperatures. A maximum growth rate of about 0.65 Å/cycle was observed at lower temperatures, around 60° C.

In some embodiments, an $Sb_2Te_3$ thin film is deposited on a substrate and forms the active material in a PCM cell. The $Sb_2Te_3$ thin film preferably has a thickness of about 10 Å to about 2000 Å.

Example 1

Sb—Te thin films were formed using alternating and sequential pulses of $SbCl_3$ and $Te(SiMe_2{}^tBu)_2$. Pulse and purge lengths were 1 and 2 seconds for $SbCl_3$ and 1 and 4 seconds for $Te(SiMe_2{}^tBu)_2$. Sb—Te thin films were grown at approximately 100° C. on a silicon surface, soda lime glass, and rhodium. The Sb—Te thin films were deposited to a thickness between about 9 nm and about 12 nm.

The morphology of each film was compared using FESEM (field emission scanning electron microscope) images. In the FESEM images there were visible isolated islands on the film formed on the silicon substrate. However, the films grown on soda lime glass and rhodium were continuous.

Example 2

Figure 3:
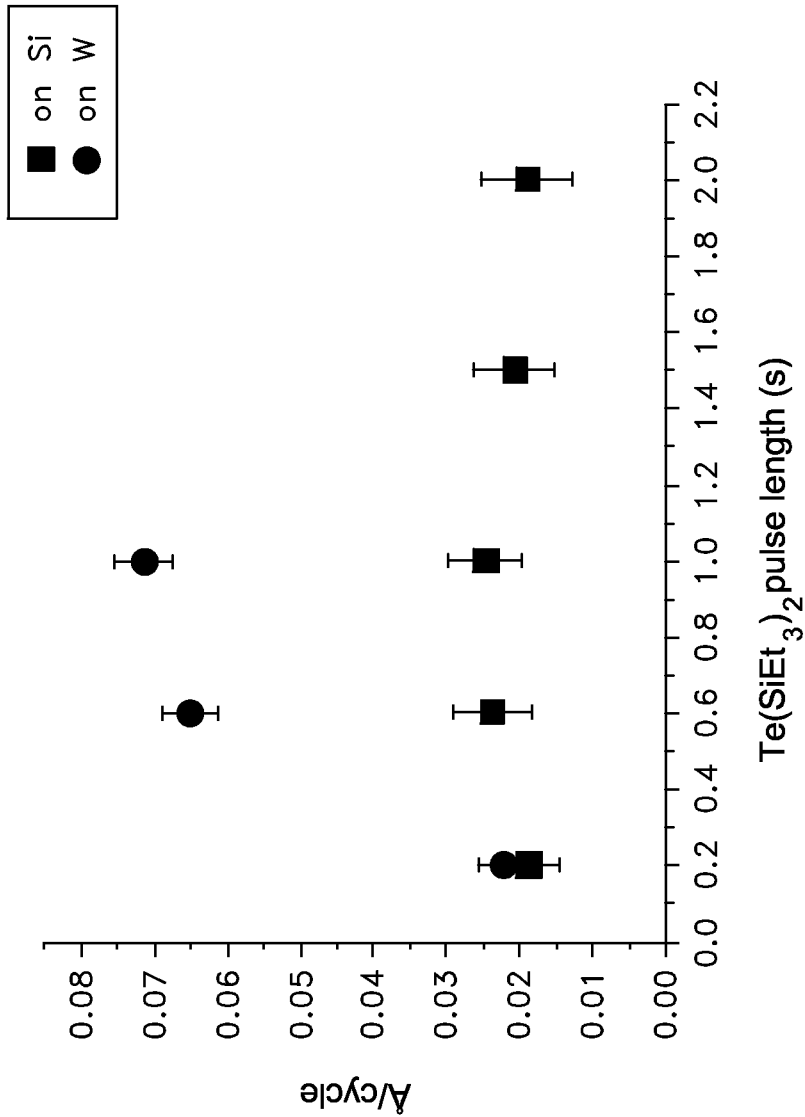
FIG. 3 is a graph of the average deposited thickness of a Sb—Te film on silicon with native oxide and on tungsten per cycle versus Te precursor pulse length.
Figure 4:
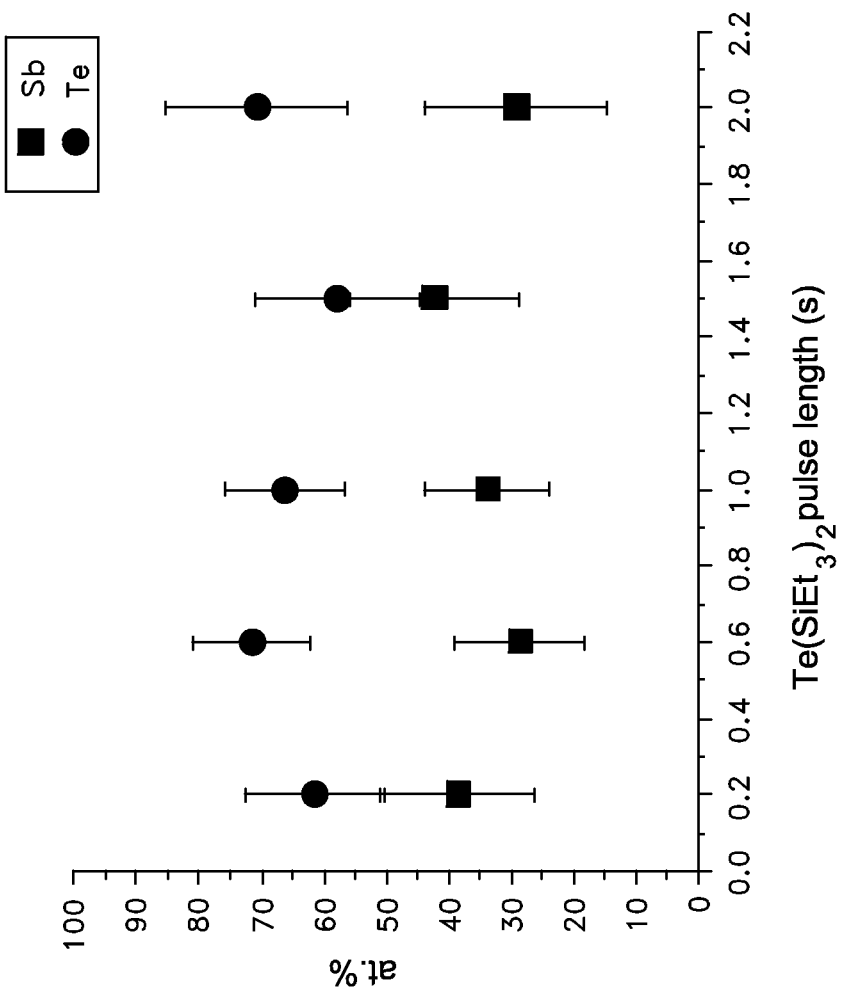
FIG. 4 is a graph of the composition of a Sb—Te film on silicon with native oxide as measured by energy dispersive x-ray (EDX) analysis.
Figure 5:
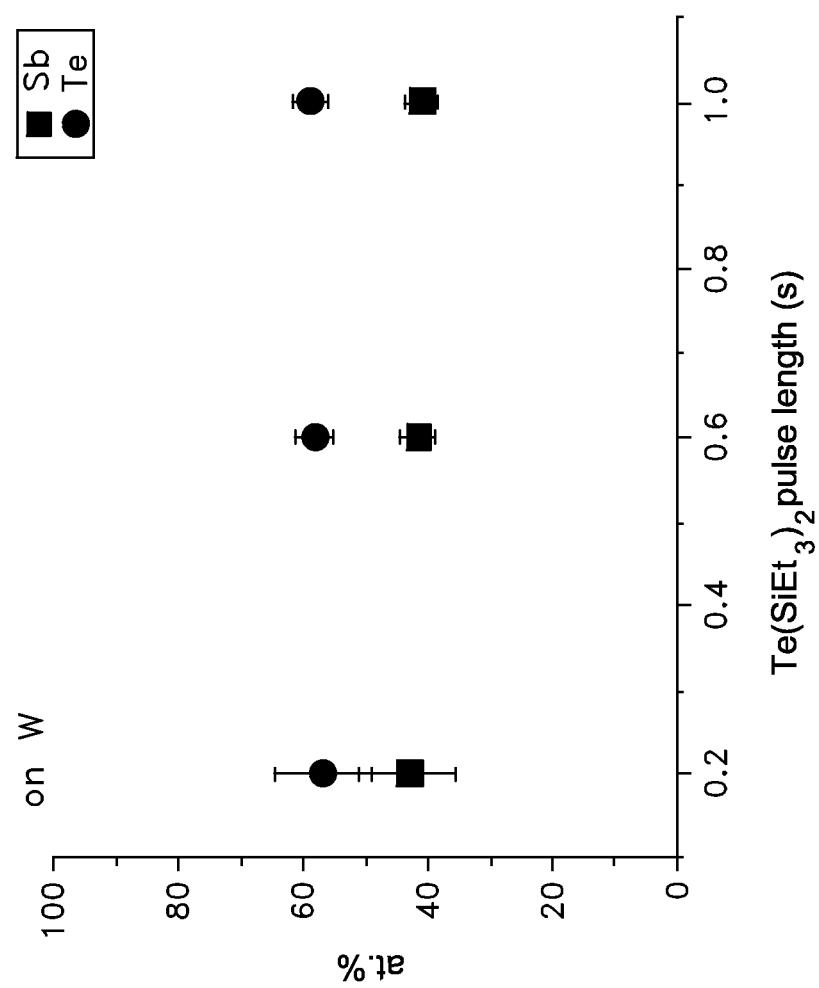
FIG. 5 is a graph of the composition of a Sb—Te film on tungsten as measured by EDX analysis.

Sb—Te films were deposited on silicon and on tungsten at approximately 150° C. using $Te(SiEt_3)_2$ as the Te source and $SbCl_3$ as the Sb source. The $SbCl_3$ pulse length was about 1 second and the purge length was about 2 seconds. The Te(SiEt$_3$)$_2$ pulse length was varied between about 0.2 seconds and 2.0 seconds while the purge length was about 2 seconds. The growth rate and composition were measured for the thin films formed with varying Te precursor pulse lengths. The results are illustrated in FIGS. 3-5, which also show error bars for each point estimating the uncertainty associated with the EDX measurement technique. As can be seen in FIG. 3, the growth rate per cycle ranged from about 0.019 to 0.025 Å/cycle on silicon with native oxide and from about 0.023 to 0.073 Å/cycle on tungsten depending on Te precursor pulse length. The exact composition of the films also varied with the pulse length of the Te precursor on silicon with native oxide (FIG. 4) and tungsten (FIG. 5).

Figure 6:
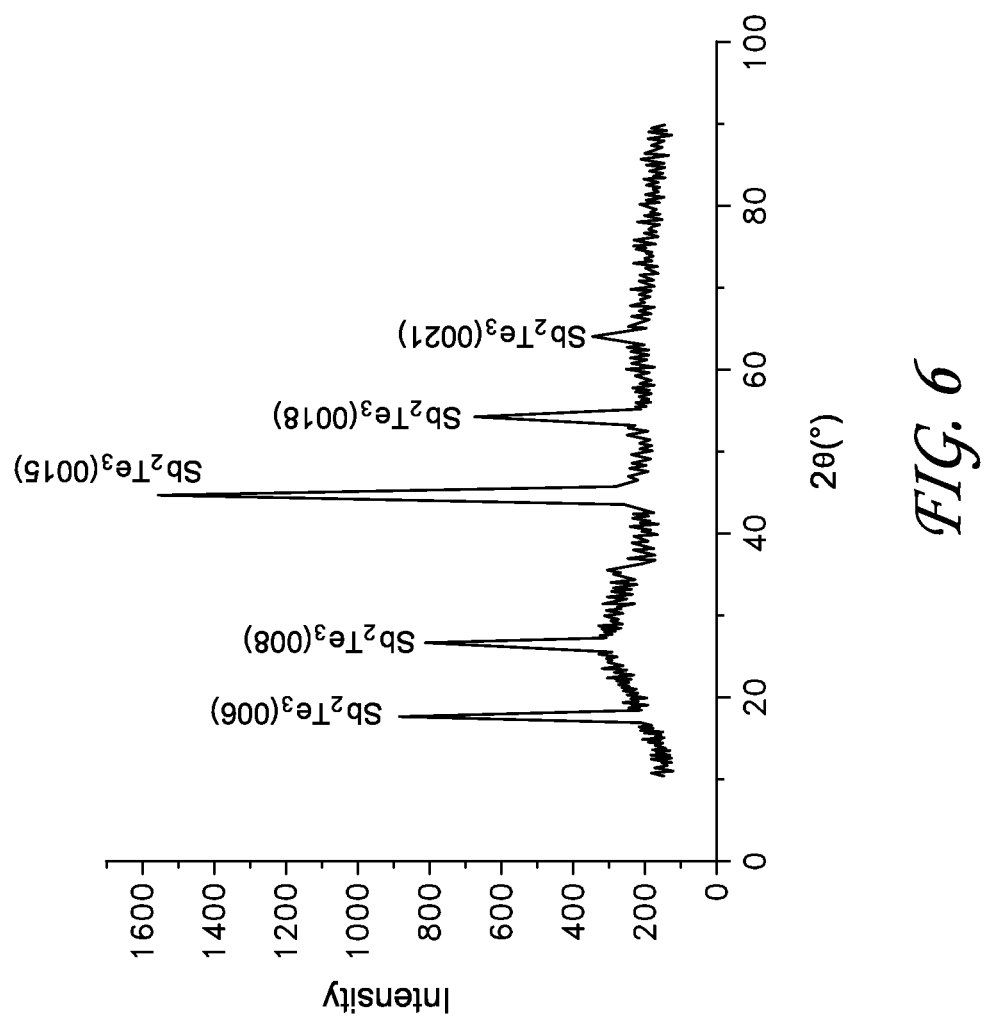
FIG. 6 is an x-ray diffractogram of a Sb—Te thin film on glass.

FIG. 6 is an x-ray diffractogram of a Sb—Te film grown on soda lime glass at 150° C. using a deposition cycle comprising:

a 1 second pulse of a SbCl$_3$;

a 2 second purge;

a 2 second pulse of Te(SiEt$_3$)$_2$; and a 2 second purge.

The Sb$_2$Te$_3$ crystalline reflections (FIG. 6) indicate a high degree of crystallinity and strong (001)-orientation in the Sb$_2$Te$_3$ thin film.

Example 3

Figure 19:
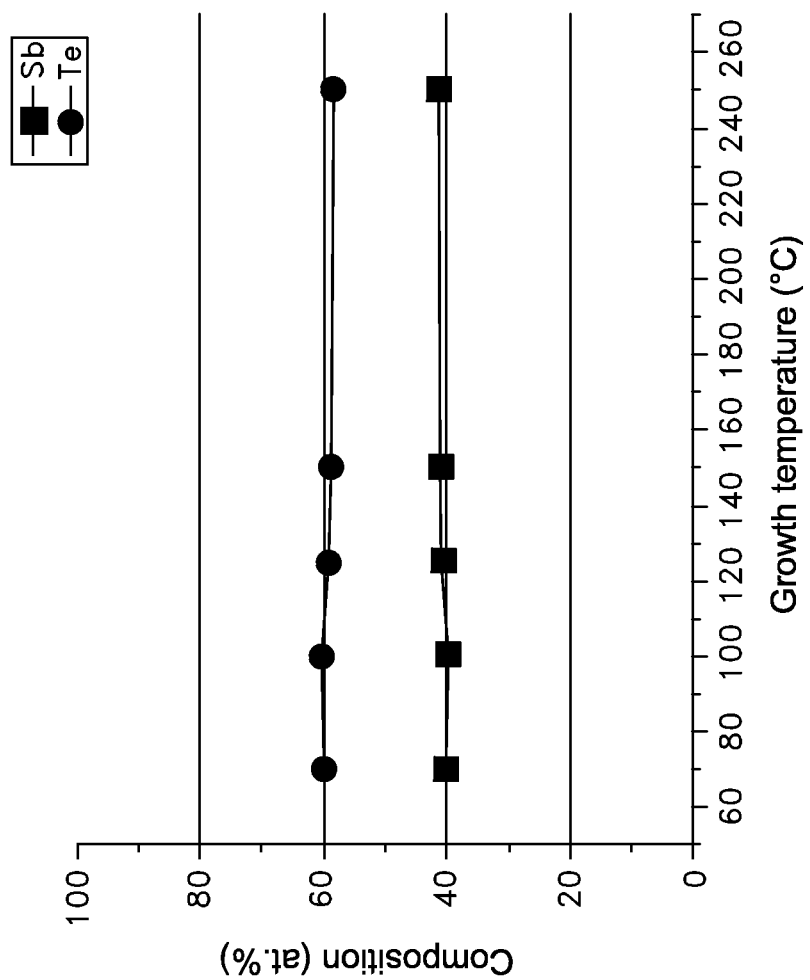
FIG. 19 is a graph of the composition of a Sb—Te thin film versus film growth temperature.

Sb—Te films were deposited on a substrate using Te(SiEt$_3$)$_2$ as the Te source and SbCl$_3$ as the Sb source at varying temperatures and varying precursor pulse lengths. FIG. 19 is a graph of the composition of a Sb—Te thin film deposited on a tungsten substrate at varying growth temperatures. The Sb—Te thin films were deposited using 1 second pulses of Te(SiEt$_3$)$_2$ and SbCl$_3$ reactants along with a 2 second purge between each reactant pulse. The deposited Sb—Te film was close to the stoichiometric ratio of Sb$_2$Te$_3$ for temperatures of about 100° C. and below. Additionally, no chlorine impurities were detected by EDX analysis. For higher temperatures, above about 120° C., the Sb—Te films contained slightly more antimony than the stoichiometric ratio of Sb$_2$Te$_3$.

Figure 20:
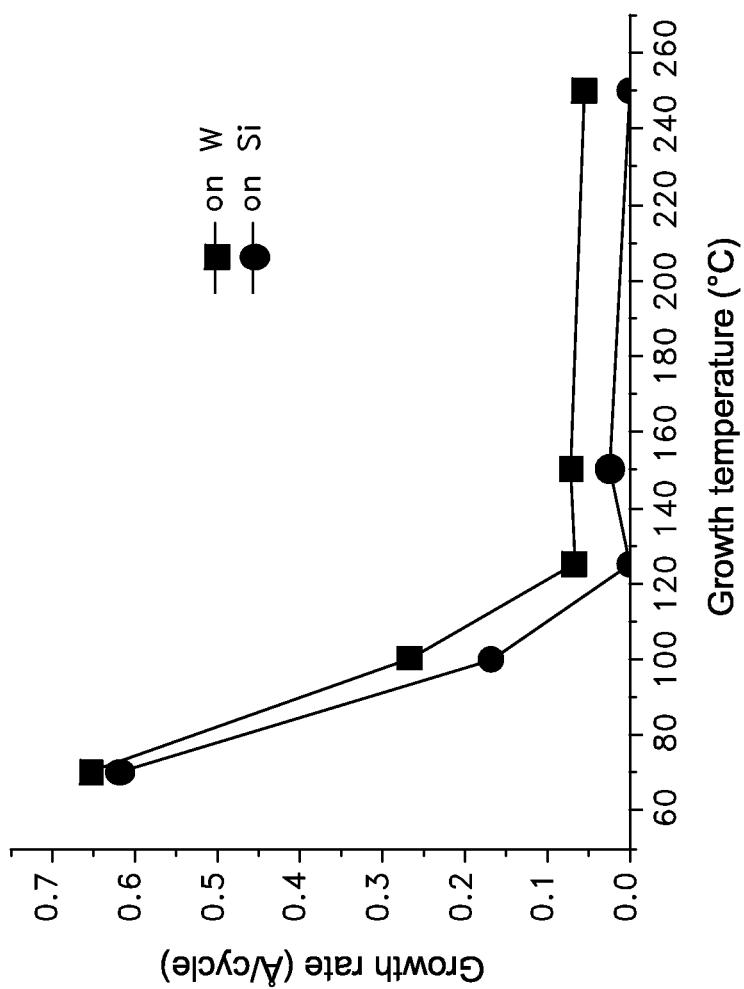
FIG. 20 is a graph of the average growth rate per cycle of a $Sb_2Te_3$ thin film versus temperature on a tungsten susbstrate and a silicon substrate.

FIG. 20 is a graph of the average growth rate per cycle of Sb—Te versus the growth temperature for Sb—Te deposited on a tungsten substrate and a silicon substrate. The Sb—Te thin films were deposited using 1 second pulses of Te(SiEt$_3$)$_2$ and SbCl$_3$ reactants along with a 2 second purge between each reactant pulse. The observed growth rate was higher at lower temperatures, with a maximum average growth rate of about 0.65 Å/cycle at a temperature of about 70° C. The growth rate decreased to below 0.1 Å/cycle at substrate temperatures above about 120° C. The growth rate on tungsten and silicon substrates exhibited similar trends, however, the growth rate observed on tungsten was slightly higher.

Figure 21:
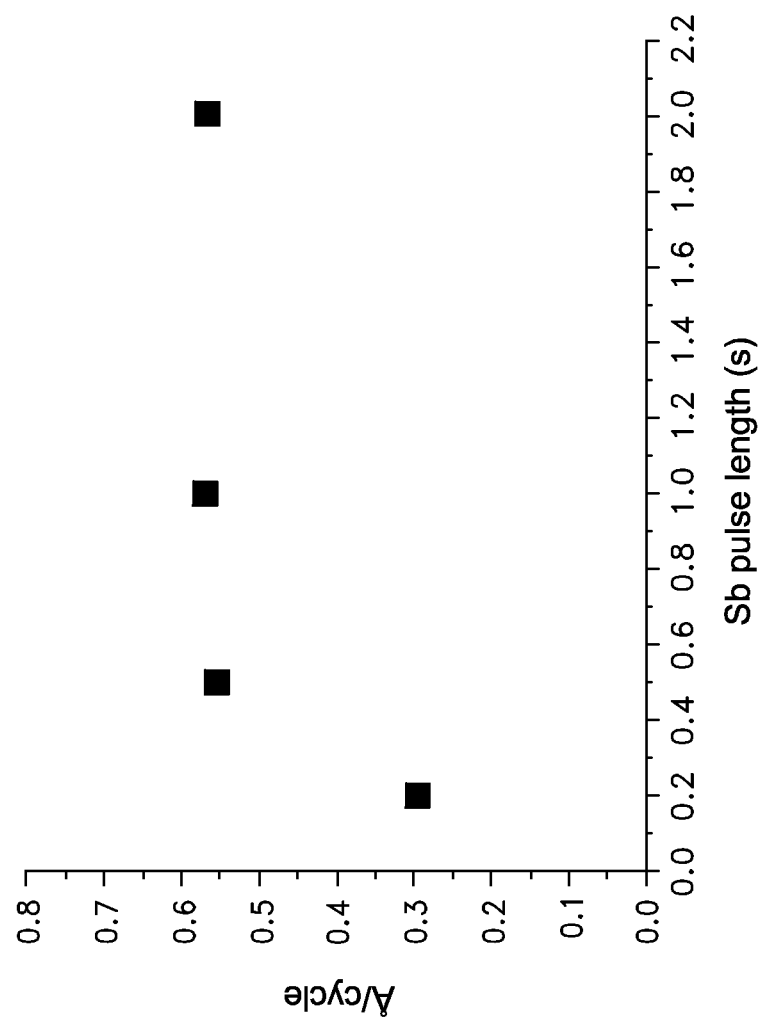
FIG. 21 is a graph of the growth rate per cycle of $Sb_2Te_3$ thin film versus the pulse length of a Sb-precursor.
Figure 22:
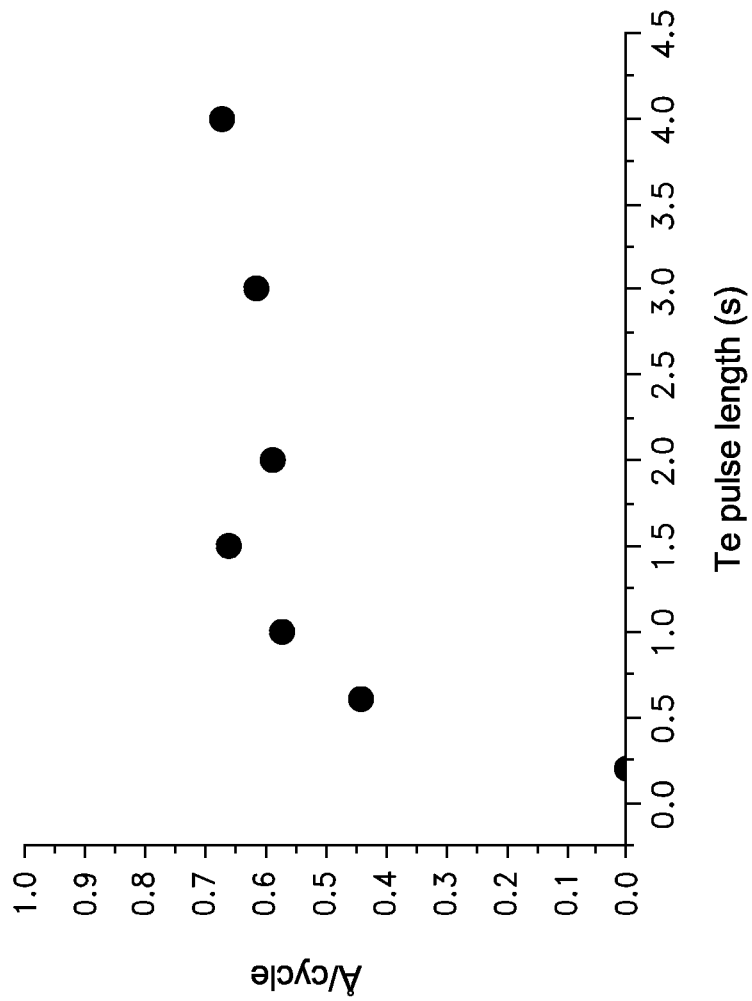
FIG. 22 is a graph of the growth rate per cycle of $Sb_2Te_3$ thin film versus the pulse length of a Te-precursor.

FIGS. 21 and 22 are graphs of the average growth rates per cycle for the deposition of Sb—Te thin films on silicon substrates varying the Sb and Te pulse lengths, respectively. SbCl$_3$ and Te(SiEt$_3$)$_2$ were used as the Sb and Te sources, respectively. The thin films were deposited at a temperature of 60° C. A pulse length of 1 second was used for the reactant that was not varied. The purge length between precursor pulses was 2 seconds. Both graphs illustrate a saturating growth rate of about 0.6 Å/cycle.

Example 4

Sb—Te films were deposited on silicon and on tungsten at approximately 90° C. using Te(SiMe$_3$)$_2$ as the Te source and SbCl$_3$ as the Sb source. The SbCl$_3$ pulse length was about 1 second and the purge length was about 2 seconds. The Te(SiMe$_3$)$_2$ pulse length was about 2 seconds while the purge length was about 2 seconds. SbCl$_3$ source temperature was about 30° C. and Te(SiMe$_3$)$_2$ was at room temperature, at about 22° C. After 2000 cycles films were analyzed by EDX, which revealed that the films were Sb$_2$Te$_3$.

Atomic Layer Deposition of Sb—Se

In other embodiments a Sb$_x$Se$_y$, preferably Sb$_2$Se$_3$, film can be formed essentially as described above, by using a Se precursor instead of a Te precursor. The Se precursor preferably has a formula of Se(SiR$^1$R$^2$R$^3$)$_2$, wherein R$^1$, R$^2$, and R$^3$ are alkyl groups with one or more carbon atoms. The skilled artisan can choose R$^1$, R$^2$, and R$^3$ alkyl groups based on the desired physical properties of the precursor such as volatility, vapor pressure, toxicity, etc. In some embodiments the Se precursor is Se(SiMe$_2^t$Bu)$_2$. In other embodiments the Se precursor is Se(SiEt$_3$)$_2$. The ALD process conditions for forming a Sb—Se thin film, such as temperature, pulse/purge times, etc. can be as described above for the deposition of Sb—Te films.

ALD of Ge—Te

Figure 7:
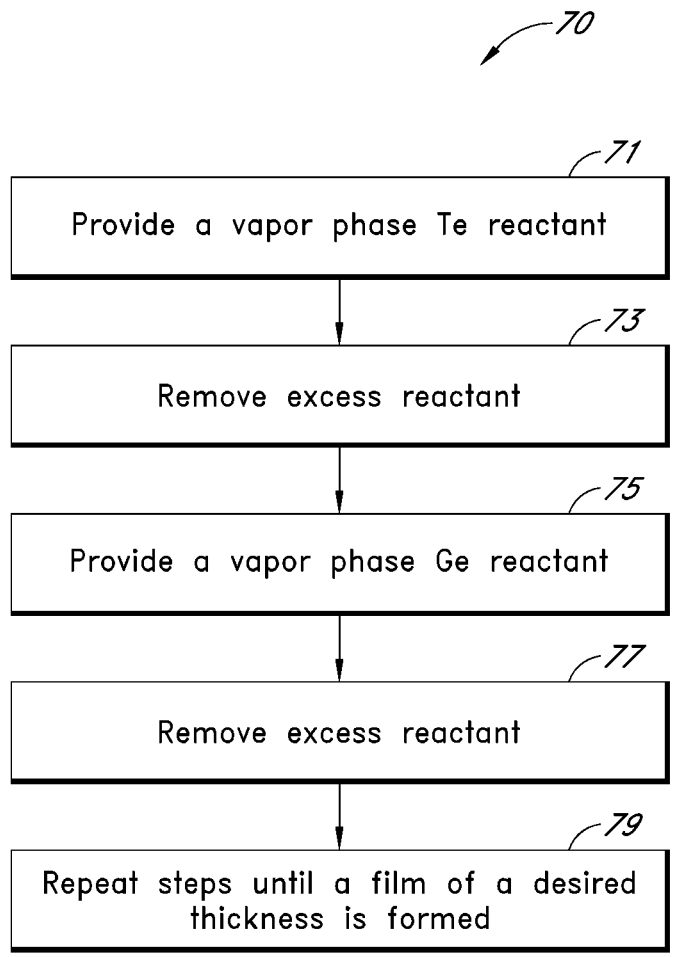
FIG. 7 is a flow chart generally illustrating a method for forming a Ge—Te film in accordance with one embodiment.

In other embodiments, a Ge$_x$Te$_y$, preferably GeTe, thin film is formed by ALD without the use of plasma. FIG. 7 is a flow chart generally illustrating a method for forming a Ge—Te thin film 70 in accordance with some embodiments. A Ge—Te thin film is formed on a substrate by an ALD type process comprising multiple Ge—Te deposition cycles, each deposition cycle comprising:

providing a first vapor phase reactant pulse comprising a Te precursor 71 into the reaction chamber to form no more than about a single molecular layer of the Te precursor on the substrate;

removing excess first reactant from the reaction chamber 73;

providing a second vapor phase reactant pulse comprising a Ge precursor 75 to the reaction chamber such that the Ge precursor reacts with the Te precursor on the substrate; and removing excess second reactant and reaction byproducts, if any, from the reaction chamber 77.

This can be referred to as the Ge—Te deposition cycle. Each Ge—Te deposition cycle typically forms at most about one monolayer of Ge—Te. The Ge—Te deposition cycle is repeated until a film of a desired thickness is formed 79. In some embodiments a Ge—Te film of from about 10 Å to about 2000 Å is formed.

Although the illustrated Ge—Te deposition cycle begins with provision of the Te precursor, in other embodiments the deposition cycle begins with the provision of the Ge precursor.

In some embodiments, the reactants and reaction by-products can be removed from the reaction chamber by stopping the flow of Te or Ge precursor while continuing the flow of an inert carrier gas such as nitrogen or argon.

Preferably, the Te precursor has a formula of Te(SiR$^1$R$^2$R$^3$)$_2$, wherein R$^1$, R$^2$, and R$^3$ are preferably alkyl groups with one or more carbon atoms. The skilled artisan can choose R$^1$, R$^2$, and R$^3$ alkyl groups based on the desired physical properties of the precursor such as volatility, vapor pressure, toxicity, etc. In some embodiments the Te precursor is Te(SiMe$_2^t$Bu)$_2$. In other embodiments the Te precursor is Te(SiEt$_3$)$_2$ or Te(SiMe$_3$)$_2$.

Preferably, the Ge source is GeX$_2$ or GeX$_4$, wherein X is a halogen element. In some embodiments the Ge source is GeBr$_2$. In some embodiments the Ge source is germanium halide with coordinating ligands, such as dioxane ligands.

Preferably the Ge source with coordinating ligands is germanium dihalide complex, more preferably a germanium dichloride dioxane complex $GeCl_2 \cdot C_4H_8O_2$.

The substrate temperature during deposition of the Ge—Te thin film is preferably less than about 300° C. and more preferably less than about 200° C. and even more preferably less than about 150° C. When $GeBr_2$ is used as the Ge precursor the process temperature is typically above about 130° C.

In some embodiments, however, the substrate temperature during deposition of the Ge—Te thin film is preferably less than 130° C. For example, when a germanium halide with coordinating ligands, such as $GeCl_2$—$C_4H_8O_2$ (germanium chloride dioxane) is used as the Ge precursor the process temperature can be as low as about 90° C. The vaporization temperature of $GeCl_2$—$C_4H_8O_2$ is around 70° C., which can allow deposition temperatures as low as about 90° C.

The skilled artisan can determine the reactant pulse times based on the properties of the selected precursors, the other reaction conditions and the desired properties of the deposited thin film. Preferably the Te and Ge reactant pulses are from about 0.05 to 10 seconds, more preferably the reactant pulses are from about 0.2 to 4 seconds, and most preferably the reactant pulses are from about 1 to 2 seconds in length. The purge steps are preferably about 0.05 to 10 seconds, more preferably about 0.2-4 seconds, and most preferably about 1 to 2 seconds in length.

The growth rate of the Ge—Te thin film may vary depending on the reaction conditions, including the length of the precursor pulses. As discussed below, in initial experiments a growth rate of around 0.15 Å/cycle was observed on silicon with native oxide with substrate temperatures around 150° C.

Example 5

Ge—Te thin films were deposited on silicon with native oxide and glass substrates at approximately 150° C. using $Te(SiEt_3)_2$ as the Te source and $GeBr_2$ as the Ge source.
 a 1 second $GeBr_2$ pulse;
 a 2 second purge;
 a 1 second $Te(SiEt_3)_2$ pulse; and
 a 2 second purge.

Figure 8:
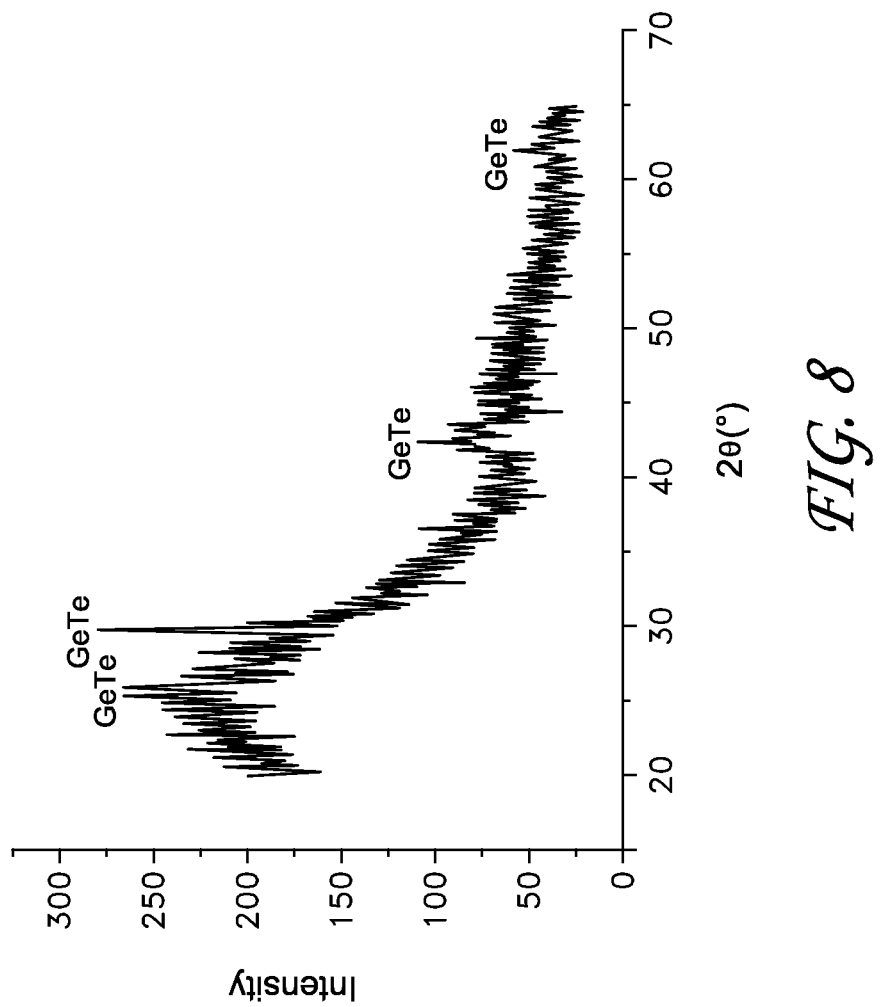
FIG. 8 is a gracing incidence x-ray diffractogram of a Ge—Te thin film on glass.

The growth rate per cycle was calculated at about 0.15 Å/cycle. FIG. 8 illustrates x-ray diffractogram results for a GeTe film on glass, indicating that the film was weakly crystalline. Energy dispersive x-ray (EDX) analysis showed that the films were slightly germanium rich at about 56% to about 58% Ge and 42% to 44% tellurium.

Example 6

Ge—Te thin films were deposited on substrates at approximately 90° C. using $Te(SiEt_3)_2$ as the Te source and $GeCl_2$—$C_4H_8O_2$ as the Ge source.
 a 1 second $GeCl_2$—$C_4H_8O_2$ pulse;
 a 2 second purge;
 a 1 second $Te(SiEt_3)_2$ pulse; and
 a 2 second purge.

The growth rate per cycle was calculated at about 0.42 Å/cycle, which is higher than the growth rate achieved with $GeBr_2$. X-ray diffractogram results indicated that the thin film comprised rhombohedral GeTe along with a noticeable fraction of amorphous phase GeTe. Energy dispersive x-ray (EDX) analysis showed that the films were slightly germanium rich at about 54% Ge and 46% tellurium.

Example 7

Ge—Te films were deposited on silicon and on tungsten at approximately 90° C. using $Te(SiMe_3)_2$ as the Te source and $GeCl_2$—$C_4H_8O_2$ as the Ge source. The $GeCl_2$—$C_4H_8O_2$ pulse length was about 1 second and the purge length was about 2 seconds. The $Te(SiMe_3)_2$ pulse length was about 2 seconds while the purge length was about 2 seconds. $GeCl_2$—$C_4H_8O_2$ source temperature was about 70° C. and $Te(SiMe_3)_2$ was at room temperature, at about 22° C. After 1000 cycles, films were analyzed by EDX, which revealed that the films were GeTe.

ALD of GeSe

In other embodiments a $Ge_xSe_y$, preferably GeSe film can be formed essentially as described above, but using a Se precursor instead of a Te precursor. The Se precursor preferably has a formula of $Se(SiR^1R^2R^3)_2$, wherein $R^1$, $R^2$, and $R^3$ are preferably alkyl groups with one or more carbon atoms. The skilled artisan can choose $R^1$, $R^2$, and $R^3$ alkyl groups based on the desired physical properties of the precursor such as volatility, vapor pressure, toxicity, etc. In some embodiments the Se precursor is $Se(SiMe_2{}^tBu)_2$. In other embodiments the Se precursor is $Se(SiEt_3)_2$. The ALD process conditions for forming a GeSe thin film, such as temperature, pulse/purge times, etc. can be selected by the skilled artisan based on routine experimentation and are essentially as described above for forming GeTe thin films.

ALD of Ge—Sb—Te

According to some embodiments, $Ge_xSb_yTe_z$, preferably $Ge_2Sb_2Te_5$, (GST) thin films are formed on a substrate by an ALD type process comprising multiple deposition cycles. In particular, a number of Ge—Te and Sb—Te deposition cycles are provided to deposit a GST film with the desired stoichiometry and the desired thickness. The Ge—Te and Sb—Te cycles can be as described above. The skilled artisan will appreciate that multiple Sb—Te deposition cycles can be performed consecutively prior to a Ge—Te cycle, and that multiple Ge—Te deposition cycles can be performed consecutively prior to a subsequent Sb—Te deposition cycle. The particular ratio of cycles can be selected to achieve the desired composition. In some embodiments the GST deposition process begins with a Ge—Te deposition cycle and in other embodiments the GST deposition process begins with an Sb—Te deposition cycle. Similarly, the GST deposition process may end with a Ge—Te deposition cycle or a Sb—Te deposition cycle.

In some preferred embodiments, the Sb—Te and Ge—Te cycles are provided in a 1:1 ratio, meaning they are alternately performed. In other embodiments, the ratio of Sb—Te cycles to the total number of cycles (Ge—Te and Sb—Te cycles combined) is selected such that the compositions of Ge and Sb in the deposited GST thin film are approximately the same. In some embodiments the ratio of Sb—Te cycles to Ge—Te cycles can be between about 100:1 and 1:100.

Figure 9:
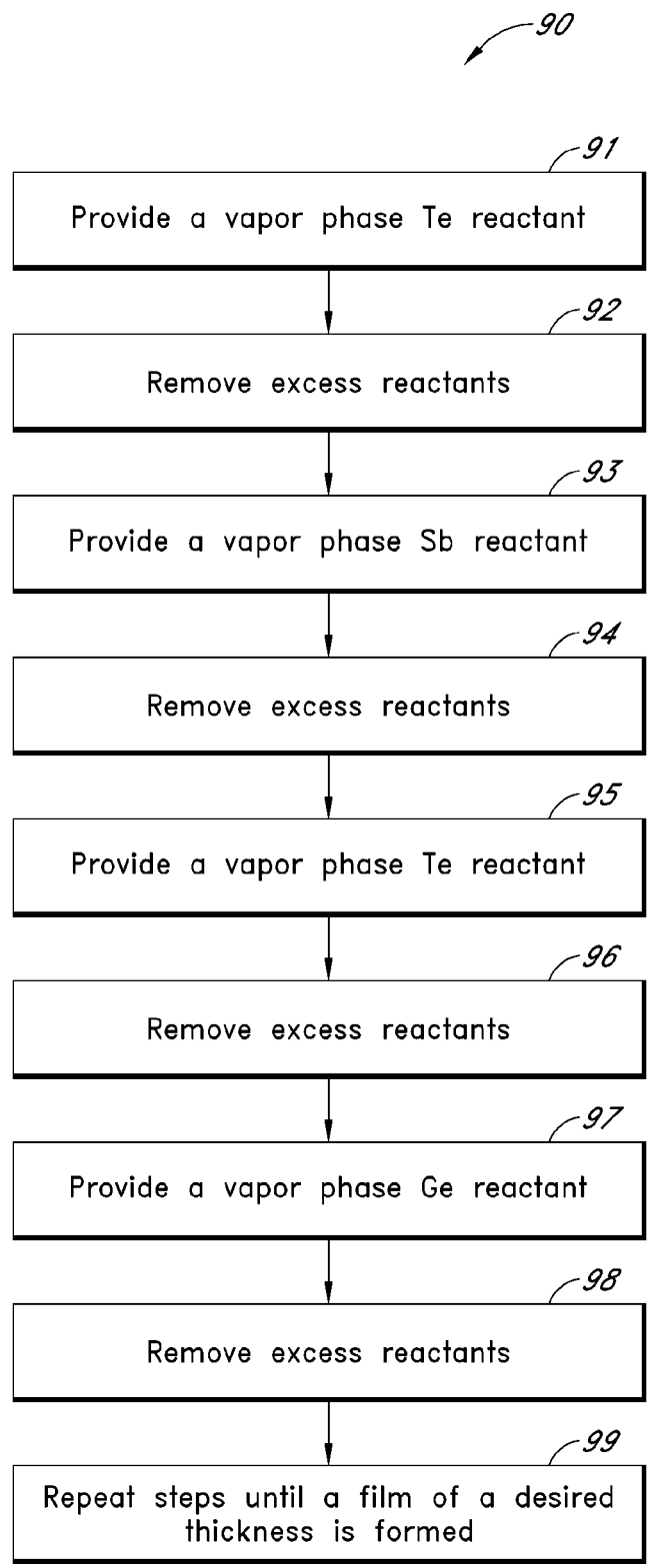
FIG. 9 is a flow chart generally illustrating a method for forming a Ge—Sb—Te film in accordance with one embodiment.

FIG. 9 is a flow chart generally illustrating a method for forming a Ge—Sb—Te (GST) thin film 90 in accordance with one such embodiment. As illustrated in FIG. 9 the method comprises:
 providing a first vapor phase reactant pulse comprising a Te precursor 91 into the reaction chamber to form no more than about a single molecular layer of the Te precursor on the substrate;
 removing excess first reactant from the reaction chamber 92;
 providing a second vapor phase reactant pulse comprising an Sb precursor 93 to the reaction chamber such that the Sb precursor reacts with the Te precursor on the substrate;
 removing excess second reactant and reaction byproducts, if any, from the reaction chamber 94;

providing a third vapor phase reactant pulse comprising a Te precursor 95 into the reaction chamber to form no more than about a single molecular layer of the Te precursor on the substrate;

removing excess third reactant from the reaction chamber 96;

providing a fourth vapor phase reactant pulse comprising a Ge precursor 97 to the reaction chamber such that the Ge precursor reacts with the Te precursor on the substrate;

removing excess fourth reactant and reaction byproducts, if any, from the reaction chamber 98.

The providing and removing steps are repeated until a film of a desired thickness is formed 99.

The process conditions, precursors, and pulse/purge times are substantially similar to those discussed above.

In some embodiments the GST thin film can be crystalline as deposited. In other embodiments an amorphous GST thin film is deposited. In some embodiments, the amorphous thin film can be annealed in the presence of an inert gas, such as nitrogen. The substrate and thin film can also be heated during the annealing step at a temperature above the deposition temperature. Preferably, the substrate temperature during the annealing step is above about 130° C. More preferably, the substrate temperature during the annealing step is above about 250° C. Most preferably the temperature during the annealing step is above 300° C. The annealing step can change the crystallinity of the thin film. In some embodiments an amorphous thin film can crystallize during the annealing step. In some embodiments the crystallinity of a crystalline GST thin film can change during the annealing step.

Example 8

A Ge—Sb—Te thin film was formed on a substrate by alternating ALD cycles of Sb—Te and Ge—Te. The ratio of Sb—Te:Ge—Te ALD cycles was 1:1. The substrate temperature was about 150° C. The reactants and pulse and purge lengths were as follows:

| | |
|---|---|
| $SbCl_3$ | 1 second; |
| Purge | 2 seconds; |
| $Te(SiEt_3)_2$ | 1 second; |
| Purge | 2 seconds; |
| $GeBr_2$ | 0.2 to 2 seconds (varied) |
| Purge | 2 seconds; |
| $Te(SiEt_3)_2$ | 1 second; and |
| Purge | 2 seconds. |

Figure 10:
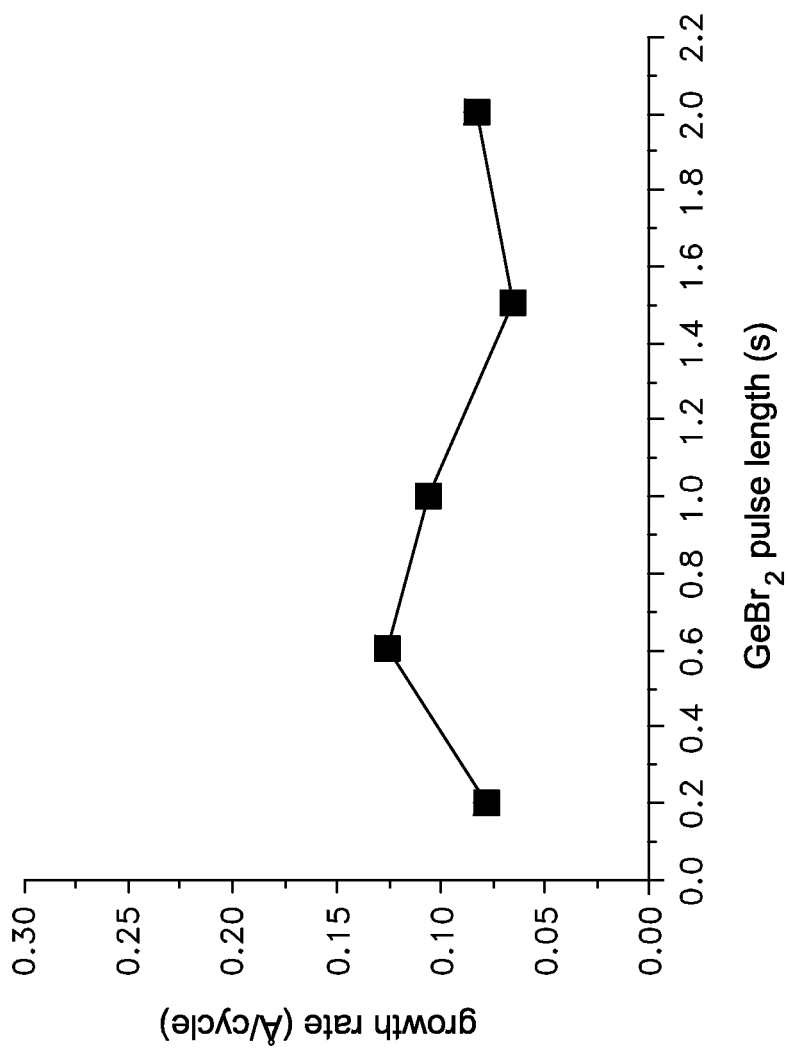
FIG. 10 is a graph of the average deposited thickness of a Ge—Sb—Te film per cycle versus Ge precursor pulse length.
Figure 11:
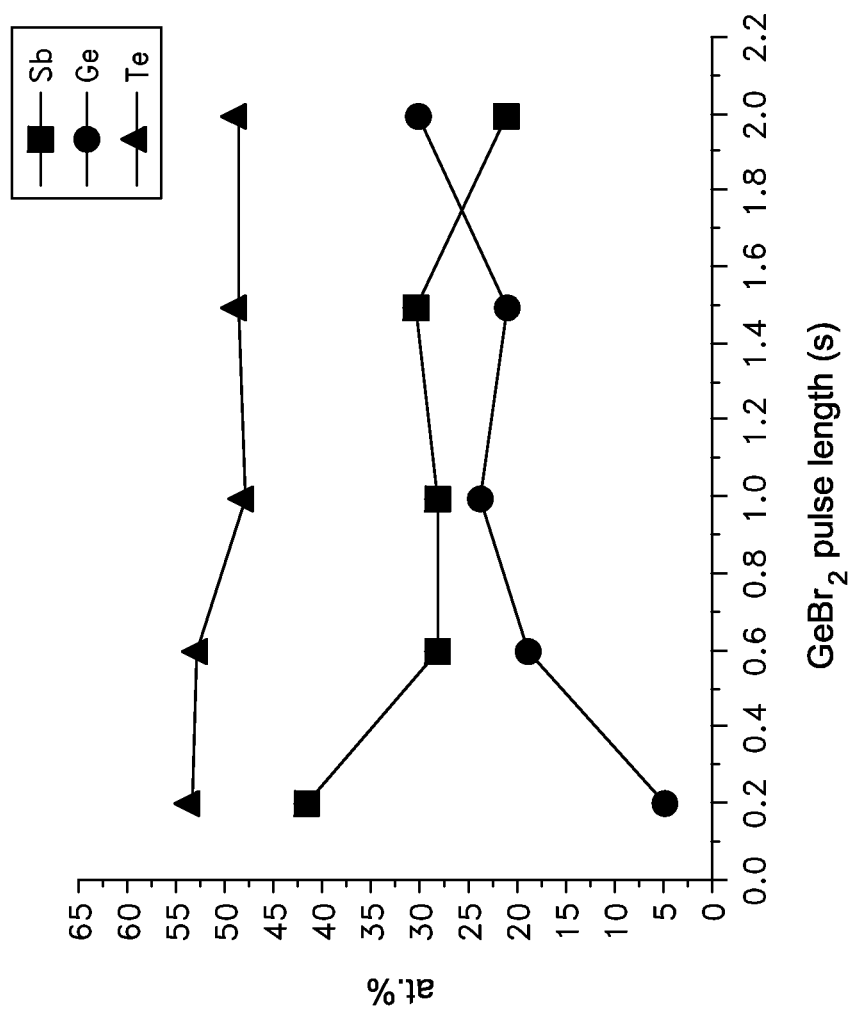
FIG. 11 is a graph of the composition of a Ge—Sb—Te film as measured by EDX analysis.

Results from these experiments are shown in FIGS. 10-13. FIG. 10 illustrates the average deposition thickness per cycle calculated by dividing the overall film thickness by the number of $Te(SiEt_3)_2$ pulses. The film thickness deposited per cycle varied between 0.05 and 0.15 Å/cycle. FIG. 11 illustrates the atomic composition of the deposited Ge—Sb—Te thin films. The Ge—Sb—Te composition is close to stoichiometric for $GeBr_2$ pulse lengths between 0.6 and 2.0 seconds. These results indicate that Sb—Te deposition is more efficient on Ge—Te than on Sb—Te alone as the film growth rate was around 0.025 Å/cycle for Sb—Te alone.

Figure 12:
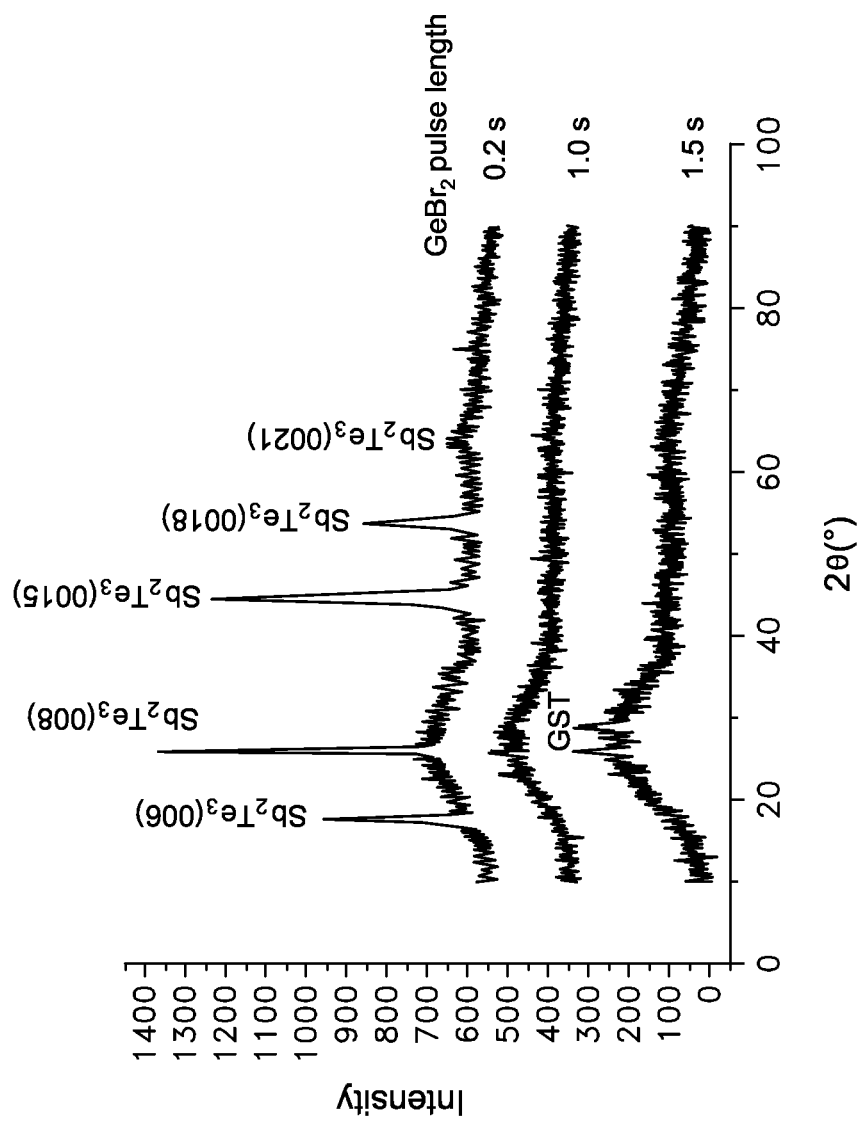
FIG. 12 is a collection of x-ray diffractograms of several Ge—Sb—Te thin films on glass formed with varying Ge precursor pulse lengths.

The morphology and crystal structure of the Ge—Sb—Te thin films also varied depending on the $GeBr_2$ pulse lengths. FIG. 12 shows an x-ray diffractogram for Ge—Sb—Te thin films formed with 0.2 s, 1.0 s, and 1.5 s pulses of $GeBr_2$. The film formed with 0.2 second pulses of $GeBr_2$ shows a crystalline structure with peaks corresponding to the $Sb_2Te_3$ crystalline structures. As the pulse length of $GeBr_2$ increases the film developed a crystalline structure closer to Ge—Sb—Te.

Figure 13:
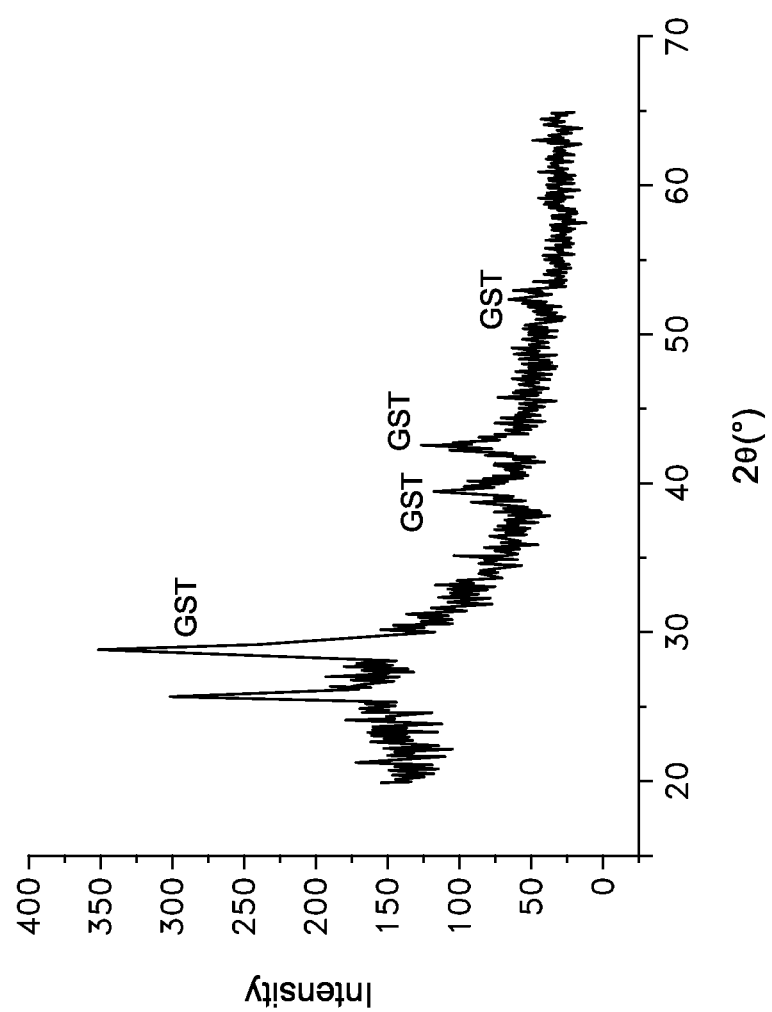
FIG. 13 is a gracing incidence x-ray diffractogram of a Ge—Sb—Te thin film on glass.

FIG. 13 shows a gracing incidence x-ray diffractogram for a film formed with 1 second pulses of $GeBr_2$. The film exhibits $Ge_2Sb_2Te_5$ crystalline reflections.

Figure 24:
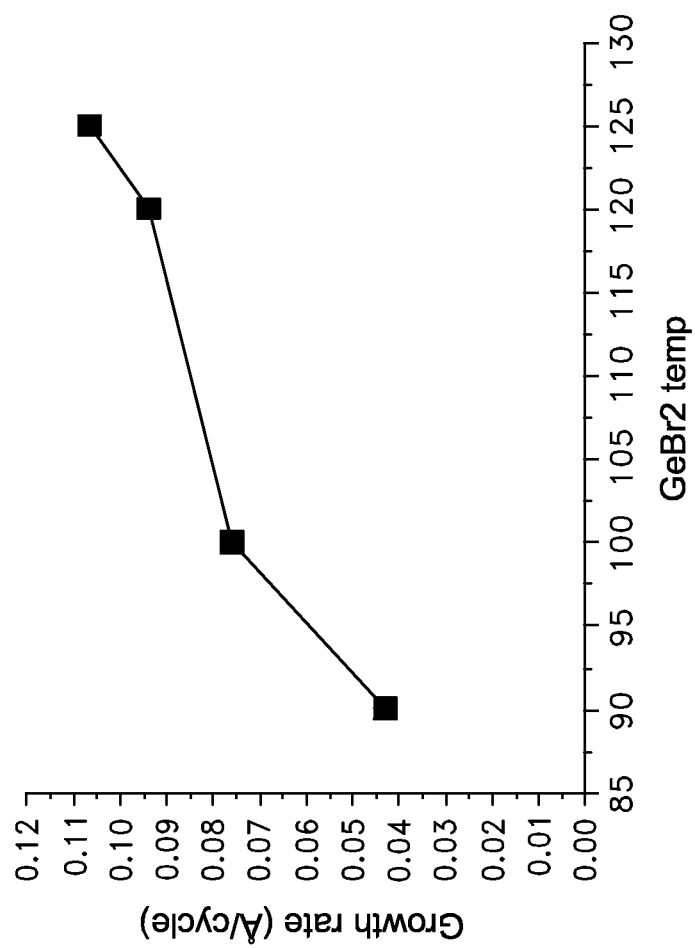
FIG. 24 is a graph of the average growth rate per cycle of a GST thin film versus the $GeBr_2$ precursor temperature.

The growth rate per cycle was also studied for various $GeBr_2$ source temperatures. The process conditions were as described above in this example, with a $GeBr_2$ pulse length of 1 second. FIG. 24 illustrates the growth rate per cycle versus $GeBr_2$ source temperatures between 90° C. and 125° C. The growth rate per cycle increases as temperature increases.

Figure 23:
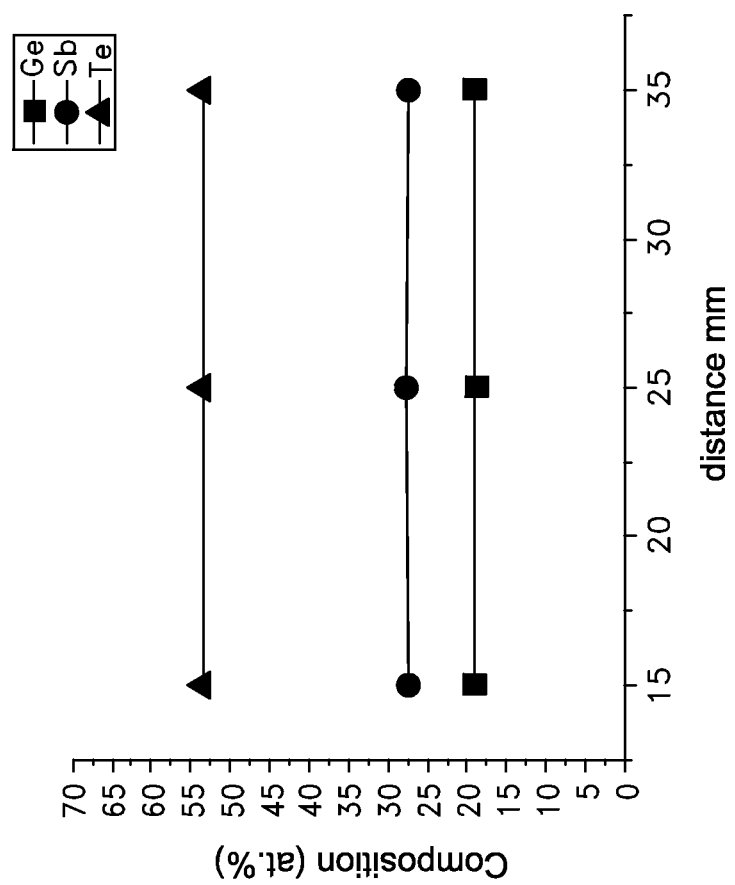
FIG. 23 is a graph of the composition of a Ge—Sb—Te (GST) thin film across the surface of a substrate.
Figure 25:
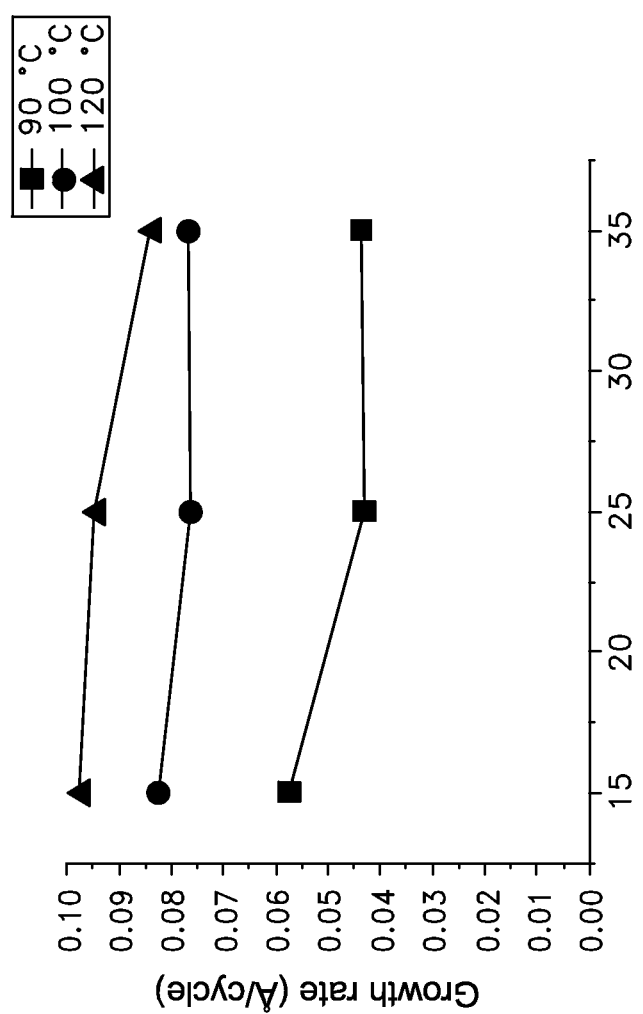
FIG. 25 is a graph of the average growth rate per cycle of a GST thin film across the substrate surface for various $GeBr_2$ precursor temperatures.

The composition of the Ge—Sb—Te thin film across the substrate was also studied. FIG. 23 is a graph of the composition of the Ge—Sb—Te thin film at various places on the substrate. The flat lines indicate that the composition of the Ge—Sb—Te thin film is consistent across the substrate. FIG. 25 is a graph of the average growth rate per cycle at different locations on the substrate for substrate deposition temperatures of 90° C., 100° C., and 120° C. The average growth rate per cycle increased with increasing temperature and varied slightly across the substrate.

Example 9

A Ge—Sb—Te thin film was formed on a substrate by alternating ALD cycles of Sb—Te and Ge—Te. The ratio of Sb—Te:Ge—Te ALD cycles was 1:1. The physical properties of $GeCl_2$—$C_4H_8O_2$ allowed for lower deposition temperatures. The reactants and pulse and purge lengths were as follows:

| | |
|---|---|
| $SbCl_3$ | 1 second; |
| Purge | 2 seconds; |
| $Te(SiEt_3)_2$ | 1 second; |
| Purge | 2 seconds; |
| $GeCl_2$—$C_4H_8O_2$ | 1-6 seconds (varied) |
| Purge | 2 seconds; |
| $Te(SiEt_3)_2$ | 1 second; and |
| Purge | 2 seconds. |

Figure 26:
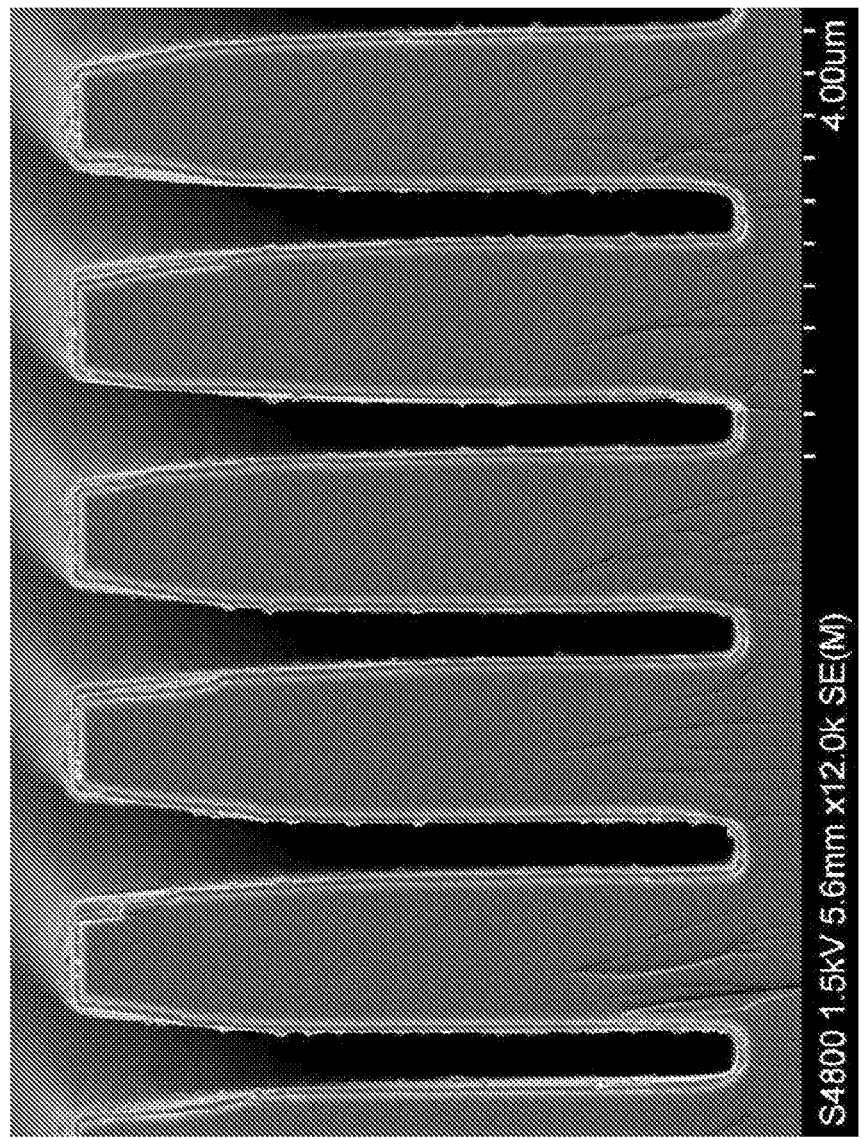
FIG. 26 is a field emission scanning electron microscope (FESEM) image of a GST thin film deposited in a high-aspect ratio trench pattern.
Figure 27:
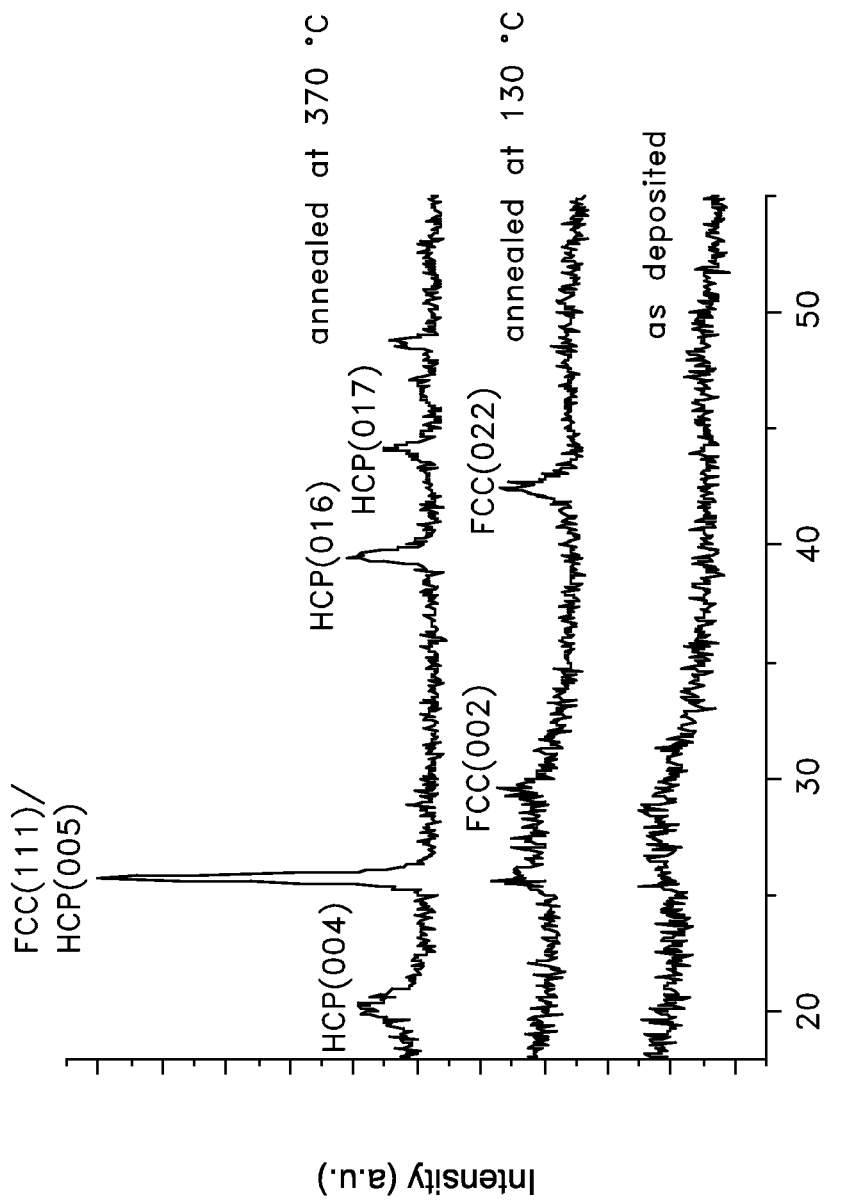
FIG. 27 is a gracing incidence X-ray diffractogram of a GST thin film.

Results from these experiments are shown in FIGS. 26-28.

FIG. 26 is a FESEM image of a GST thin films deposited in high aspect trench structures. The deposition conditions were essentially as described above in the Examples, however, a Ge—Te/(Ge—Te+$Sb_2Te_3$) cycling ratio of 0.33 was used. The FESEM image shows that the film thickness in the trench structure of about 65 nm is virtually the same in different parts of the structure. The image shows that the ALD process using these precursors is capable of depositing uniform and highly conformal thin films in high aspect ratio structures, such as trench structures.

FIG. 27 is a gracing incidence X-ray diffractogram of a GST thin film with a composition of 23% Ge, 28% Sb, and 49% Te that was subjected to high temperature XRD measurements. The GST thin film was annealed in the presence of a nitrogen flow with XRD measurements done in situ. The GST thin film was amorphous as deposited at a temperature of about 90° C. The GST thin film began to crystallize at 130° C. exhibiting reflections belonging to the meta-stable rock salt structure. As the annealing temperature increased gradually, the crystalline structure changed to the stable hexagonal phase. The cubic and hexagonal phases are clearly distinguished in FIG. 27.

Figure 28B:
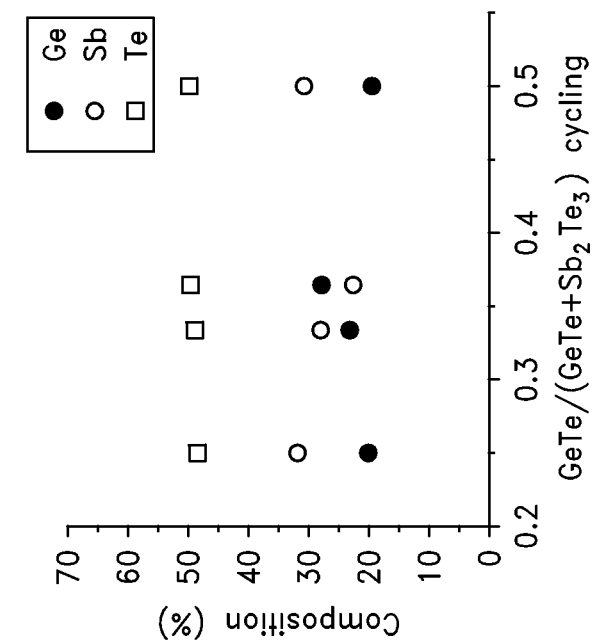
FIGS. 28A+28B are graphs of the composition of GST thin films versus $GeCl_2$-dioxane precursor pulse length and versus Ge—Te cycling ratio, respectively.
Figure 28A:
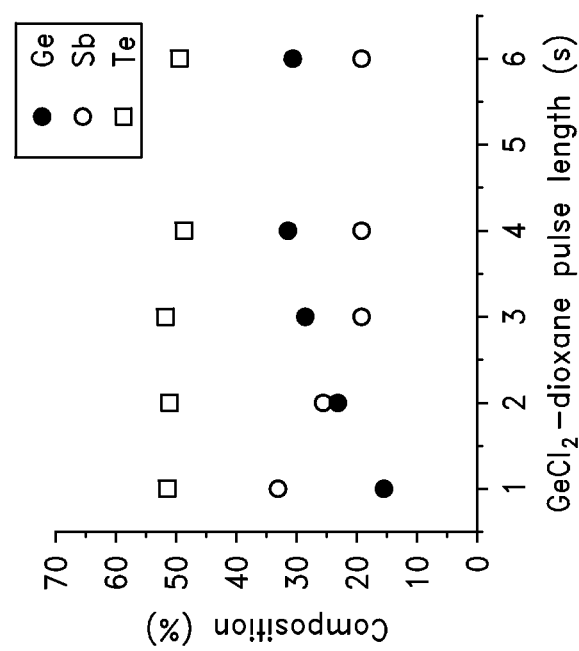

FIG. 28A illustrates the composition of a GST thin film deposited with varying pulse lengths of $GeCl_2$-dioxane. FIG. 28A shows that increasing the pulse length of $GeCl_2$-dioxane increases the amount of Ge and decreases the amount of Te in the GST thin film when $GeCl_2$-dioxane pulse length is less than about 4 seconds in the used reactor. FIG. 28A also shows that film composition saturates when GeCl$_2$-dioxane pulse length is more than about 4 seconds in the used reactor. Saturation may happen with different GeCl$_2$-dioxane pulse lengths at different reactors. FIG. 28B is a graph of the composition of various GST thin films for various Ge—Te/(Ge—Te+Sb—Te) cycling ratios. FIG. 28B shows that a cycling ratio of about 0.35 should result in a GST thin film with about equal compositions of Ge and Sb.

Example 10

Sb—Te and Ge—Sb—Te films were deposited on 200 mm silicon substrates in a Pulsar® 2000 reactor by using SbCl$_3$, Te(SiEt$_3$)$_2$ and GeCl$_2$.dioxane as a precursors at growth temperatures of 70° C. and 90° C. Precursor temperatures for SbCl$_3$, Te(SiEt$_3$)$_2$ and GeCl$_2$.dioxane were 45° C., 60° C. and 60° C., respectively. Precursor pulse times for SbCl$_3$, Te(SiEt$_3$)$_2$ and GeCl$_2$.dioxane were about 0.5 seconds, 0.5 seconds and from about 5 to about 15 seconds, respectively. Precursor purge times for SbCl$_3$, Te(SiEt$_3$)$_2$ and GeCl$_2$.dioxane were varied in the range of 1 seconds to 20 seconds. Films had full coverage with relatively good uniformity across the 200 mm wafer. EDX revealed the films to be nearly stoichiometric Sb$_2$Te$_3$ and Ge$_2$Sb$_2$Te$_5$.

ALD of Ge—Sb—Se

In other embodiments a Ge$_x$Sb$_y$Se$_z$, preferably GeSbSe film, can be formed by using a Se precursor instead of a Te precursor in the process described above for Ge—Sb—Te. The Se precursor preferably has a formula of Se(SiR$^1$R$^2$R$^3$)$_2$, wherein R$^1$, R$^2$, and R$^3$ are preferably alkyl groups with one or more carbon atoms. The skilled artisan can choose R$^1$, R$^2$, and R$^3$ alkyl groups based on the desired physical properties of the precursor such as volatility, vapor pressure, toxicity, etc. In some embodiments the Se precursor is Se(SiMe$_2$$^t$Bu)$_2$ and in other embodiments is Se(SiEt$_3$)$_2$. The ALD process conditions for forming a Ge—Sb—Se thin film are essentially as described above for forming a GST film, with an Sb—Se deposition cycle substituted for the Sb—Te deposition cycles and a Ge—Se deposition cycle substituted for the Ge—Te deposition cycles.

ALD of Bi—Te

Figure 14:
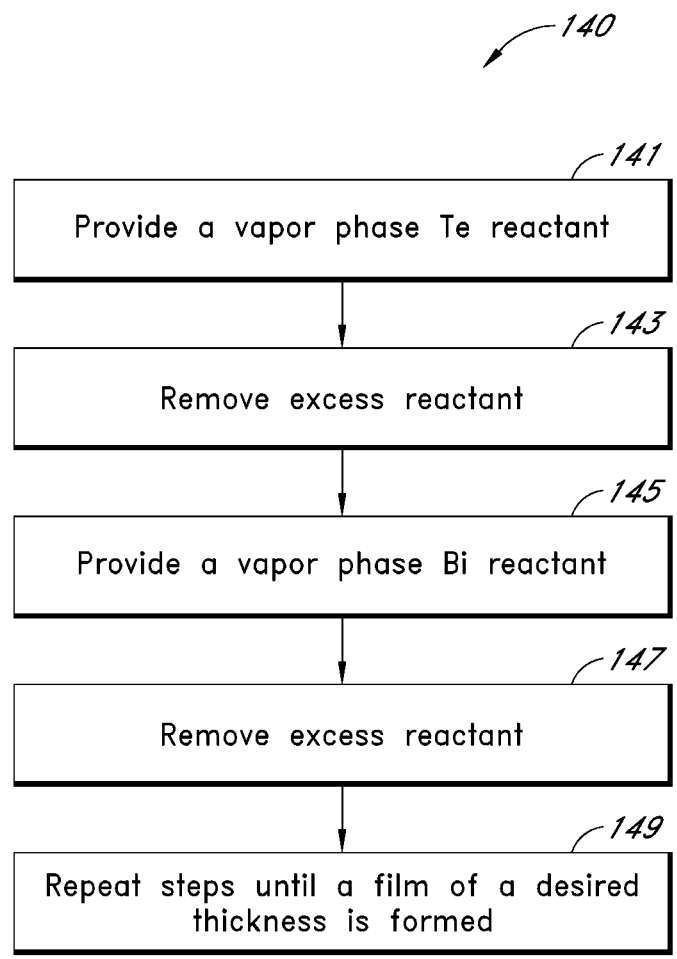
FIG. 14 is a flow chart generally illustrating a method for forming a Bi—Te film in accordance with one embodiment.

FIG. 14 is a flow chart generally illustrating methods for forming Bi—Te thin films 140 in accordance with some embodiments. A Bi$_x$Te$_y$, preferably BiTe, thin film is formed on a substrate by an ALD type process comprising multiple Bi—Te deposition cycles, each Bi—Te deposition cycle comprising:
  providing a first vapor phase reactant pulse comprising a Te precursor 141 into the reaction chamber to form no more than about a single molecular layer of the Te precursor on the substrate;
  removing excess first reactant from the reaction chamber 143;
  providing a second vapor phase reactant pulse comprising a Bi precursor 145 to the reaction chamber such that the Bi precursor reacts with the Te precursor on the substrate; and
  removing excess second reactant and reaction byproducts, if any, from the reaction chamber 147.

Each Bi—Te deposition cycle typically forms at most about one monolayer of Bi—Te. The Bi—Te deposition cycle is repeated until a film of a desired thickness is formed 149. In some embodiments a Bi—Te film of from about 10 Å to about 2000 Å is formed.

Although the illustrated Bi—Te deposition cycle begins with provision of the Te precursor, in other embodiments the deposition cycle begins with the provision of the Bi precursor.

In some embodiments, the reactants and reaction by-products can be removed from the reaction chamber by stopping the flow of Te or Bi precursor while continuing the flow of an inert carrier gas such as nitrogen or argon.

Preferably, the Te precursor has a formula of Te(SiR$^1$R$^2$R$^3$)$_2$, wherein R$^1$, R$^2$, and R$^3$ are alkyl groups comprising one or more carbon atoms. The R$^1$, R$^2$, and R$^3$ alkyl groups can be selected based on the desired physical properties of the precursor such as volatility, vapor pressure, toxicity, etc. In some embodiments the Te precursor is Te(SiMe$_2$$^t$Bu)$_2$. In other embodiments the precursor is Te(SiEt$_3$)$_2$.

Preferably, the Bi precursor has a formula of BiX$_3$, wherein X is a halogen element. In some embodiments the Bi precursor is BiCl$_3$.

The process temperature during the Bi—Te deposition cycle is preferably less than 300° C., and more preferably less than 200° C. The pulse and purge times are typically less than 5 seconds, and preferably around 1-2 seconds. The skilled artisan can choose pulse/purge times based on the particular circumstances.

Example 11

Figure 15:
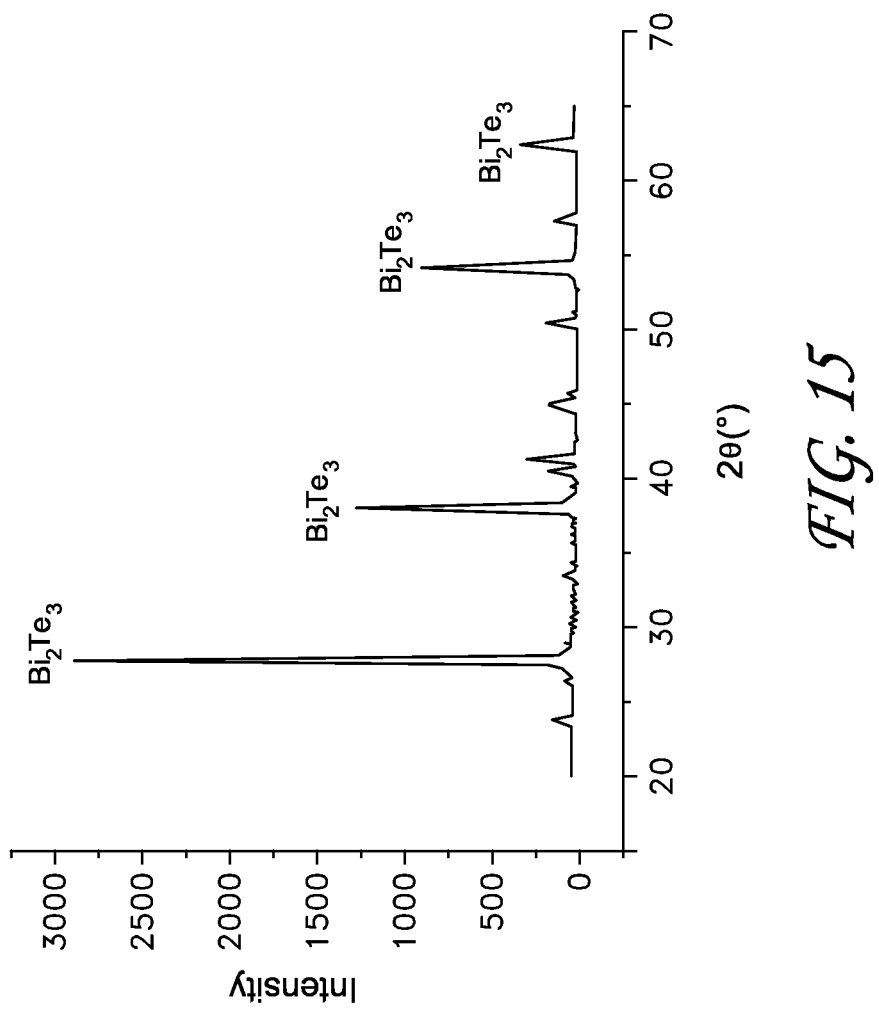
FIG. 15 is a gracing incidence x-ray diffractogram of a Bi—Te thin film.

A Bi$_2$Te$_3$ film was deposited on silicon and glass substrates at a temperature of about 175° C. using BiCl$_3$ and Te(SiEt$_3$)$_2$ precursors. The pulse and purge times of the precursors were 1 and 2 seconds, respectively. The average growth rate per cycle was about 1.2 Å/cycle. Analysis of the film showed that the film composition was close to the stoichiometric ratio for Bi$_2$Te$_3$. FIG. 15 is a gracing incidence x-ray diffractogram of the Bi$_2$Te$_3$ film, which showed that the film was crystalline and that the peaks corresponding to Bi$_2$Te$_3$ were pronounced.

ALD of Bi—Se

In other embodiments, a Bi$_x$Se$_y$, preferably BiSe film is formed by using a Se precursor instead of a Te precursor in the ALD process described above for Bi—Te. The Se precursor preferably has a formula of Se(SiR$^1$R$^2$R$^3$)$_2$, wherein R$^1$, R$^2$, and R$^3$ are preferably alkyl groups with one or more carbon atoms. The skilled artisan can choose R$^1$, R$^2$, and R$^3$ alkyl groups based on the desired physical properties of the precursor such as volatility, vapor pressure, toxicity, etc. In some embodiments the Se precursor is Se(SiMe$_2$$^t$Bu)$_2$ and in other embodiments the Se precursor is Se(SiEt$_3$)$_2$. The ALD process conditions for forming a Bi—Se thin film, such as temperature, pulse/purge times, etc. can be selected by the skilled artisan and are essentially as described above for Bi—Te.

ALD of Zn—Te

Figure 16:
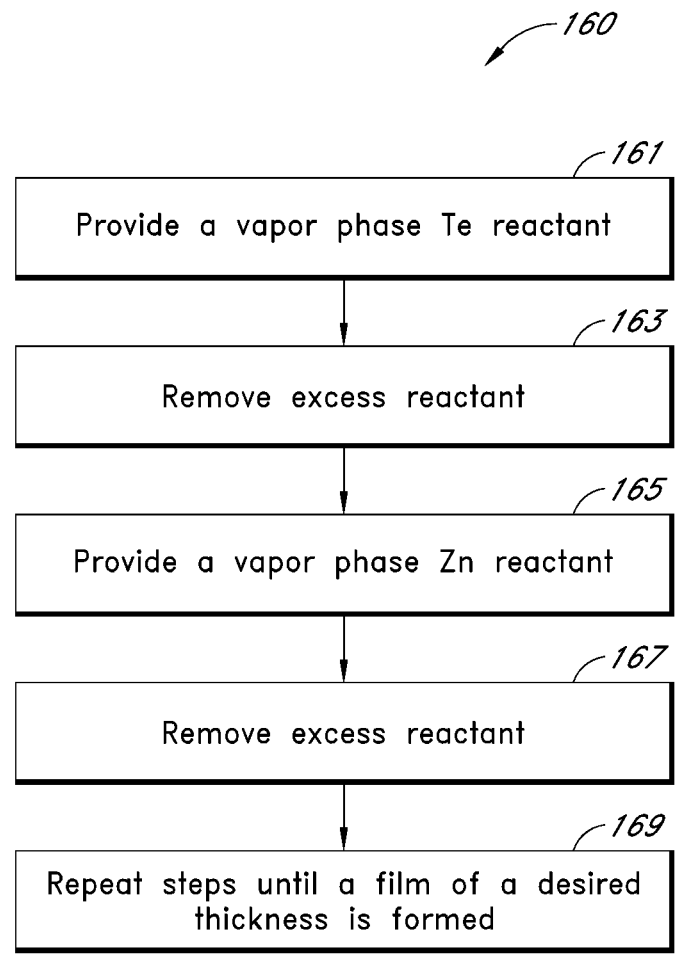
FIG. 16 is a flow chart generally illustrating a method for forming a Zn—Te film in accordance with one embodiment.

FIG. 16 is a flow chart generally illustrating methods for forming Zn—Te thin films 160. A Zn$_x$Te$_y$, preferably ZnTe, thin film can be formed on a substrate by an ALD type process comprising multiple Zn—Te deposition cycles, each Zn—Te deposition cycle comprising:
  providing a first vapor phase reactant pulse comprising a Te precursor 161 into the reaction chamber to form no more than about a single molecular layer of the Te precursor on the substrate;
  removing excess first reactant from the reaction chamber 163;
  providing a second vapor phase reactant pulse comprising a Zn precursor 165 to the reaction chamber such that the Zn precursor reacts with the Te precursor on the substrate; and
  removing excess second reactant and reaction byproducts, if any, from the reaction chamber 167.

The Zn—Te cycle is repeated until a film of a desired thickness is formed 169. In some embodiments a Zn—Te film of from about 10 Å to about 2000 Å is formed.

Although the illustrated Zn—Te deposition cycle begins with provision of the Te precursor, in other embodiments the deposition cycle begins with the provision of the Zn precursor.

In some embodiments, the reactants and reaction by-products can be removed from the reaction chamber by stopping the flow of Te or Zn precursor while continuing the flow of an inert carrier gas such as nitrogen or argon.

Preferably, the Te precursor has a formula of $Te(SiR^1R^2R^3)_2$, wherein $R^1$, $R^2$, and $R^3$ are preferably alkyl groups with one or more carbon atoms. The skilled artisan can choose $R^1$, $R^2$, and $R^3$ alkyl groups based on the desired physical properties of the precursor such as volatility, vapor pressure, toxicity, etc. In some embodiments the Te precursor is $Te(SiMe_2{}^tBu)_2$. In other embodiments the Te precursor is $Te(SiEt_3)_2$.

Preferably, the Zn precursor has a formula of $ZnX_2$, wherein X is a halogen element or an alkyl group. In some embodiments the Zn precursor is $ZnCl_2$ or $Zn(C_2H_5)_2$.

The process temperature during the Zn—Te deposition cycle is preferably less than 500° C., and more preferably about 400° C. The pulse and purge times are typically less than 5 seconds, preferably about 0.2-2 seconds, and more preferably about 0.2-1 seconds. The skilled artisan can choose appropriate pulse/purge times based on the particular circumstances.

Example 12

A Zn—Te film was deposited on a silicon with native oxide and a glass substrate at a deposition temperature of about 400° C., using alternating and sequential pulses of $ZnCl_2$ and $Te(SiEt_3)_2$. Pulse and purge lengths of 0.4 and 0.5 seconds, respectively, were used for both precursors.

Figure 17:
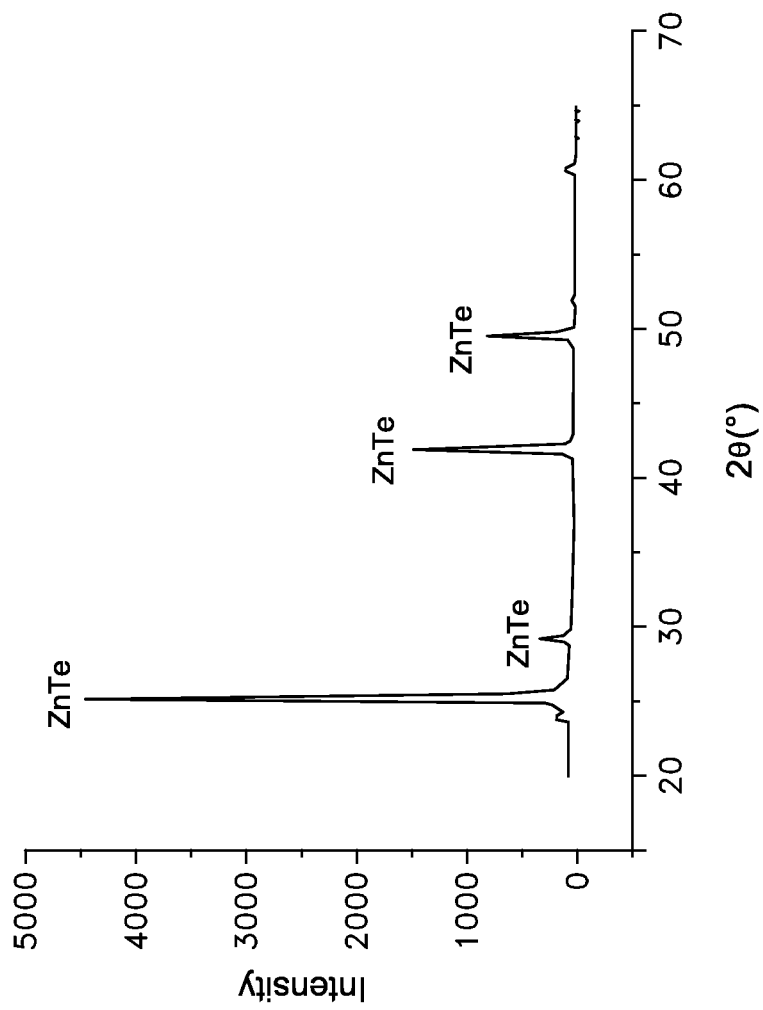
FIG. 17 is a gracing incidence x-ray diffractogram of a Zn—Te thin film.

The average growth rate per cycle was about 0.6 Å/cycle. EDX analysis of the film showed that the film was close to stoichiometric with a composition of 47% Zn and 53% Te. FIG. 17 is an x-ray diffractogram of the Zn—Te thin film that was formed, illustrating that the film was crystalline with a cubic configuration.

ALD of Zn—Se

In other embodiments a $Zn_xSe_y$, preferably ZnSe, film can be formed by using a Se precursor in place of a Te precursor in the deposition cycle outlined above. The Se precursor preferably has a formula of $Se(SiR^1R^2R^3)_2$, wherein $R^1$, $R^2$, and $R^3$ are preferably alkyl groups with one or more carbon atoms. The skilled artisan can choose $R^1$, $R^2$, and $R^3$ alkyl groups based on the desired physical properties of the precursor such as volatility, vapor pressure, toxicity, etc. In some embodiments the Se precursor is $Se(SiMe_2{}^tBu)_2$ and in other embodiments is $Se(SiEt_3)_2$. The ALD process conditions for forming a Zn—Se thin film, such as temperature, pulse/purge times, etc. can be selected by the skilled artisan and are essentially as described above for deposition of Zn—Te.

Example 13

Figure 29:
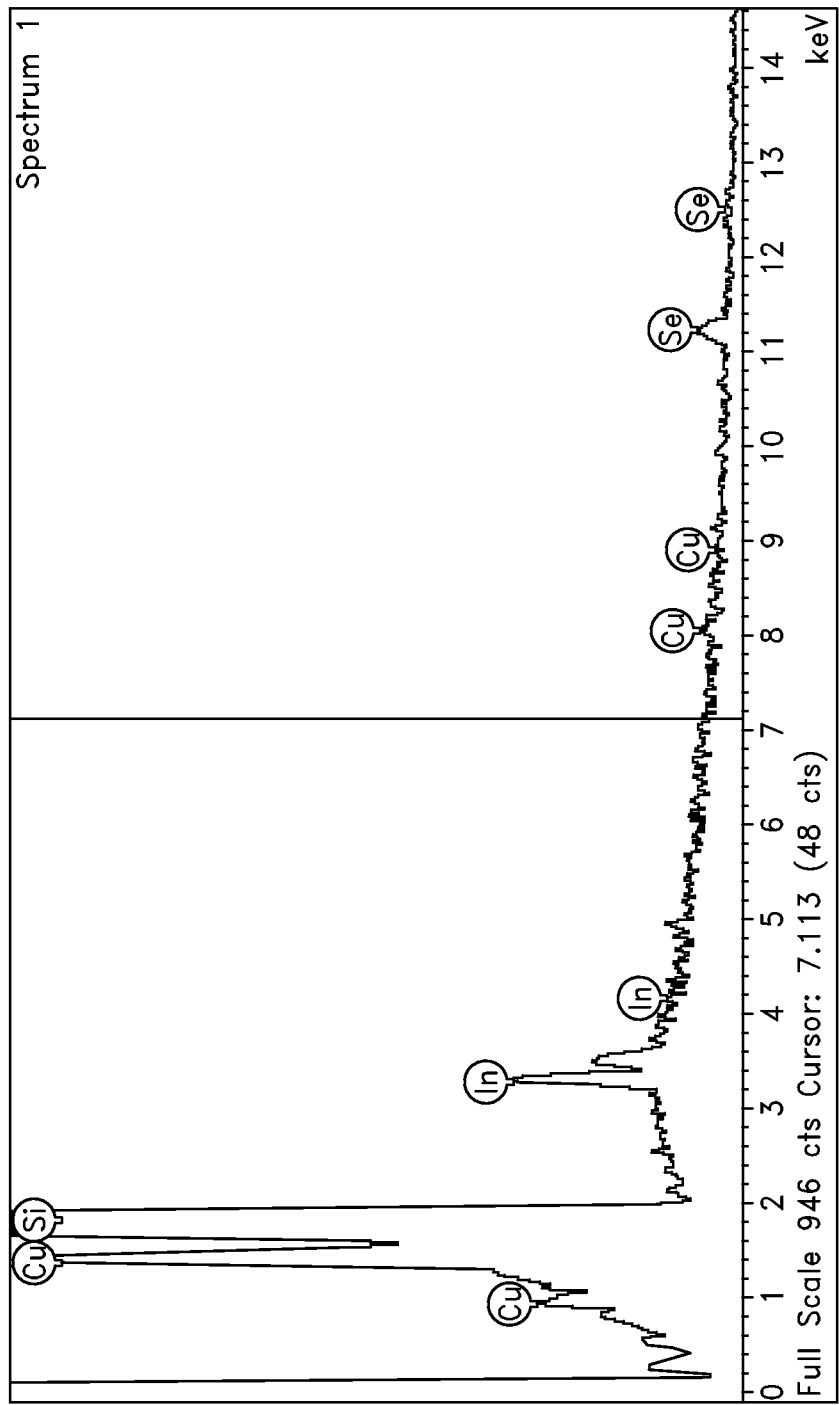
FIG. 29 is a graph of the composition of a Cu—In—Se film as measured by energy dispersive x-ray (EDX) analysis.

Cu—In—Se films were deposited on both a silicon substrate with native oxide and a glass substrate at a deposition temperature of about 340° C. using alternating and sequential pulses of reactants. The reactants were CuCl, $InCl_3$, and $Se(SiEt_3)_2$ and were at source temperatures of 325° C., 275° C. and 35° C., respectively. A Cu—Se cycle comprised alternating and sequential pulses of CuCl and $Se(SiEt_3)_2$. An In—Se cycle comprised alternating and sequential pulses of $InCl_3$ and $Se(SiEt_3)_2$. A pulsing ratio of (Cu—Se) cycles to (In—Se) cycles was 1:1. Pulse and purge lengths of 1 and 2 seconds, respectively, were used for all precursors. FIG. 29 shows an EDX analysis of the deposited Cu—In—Se film. EDX analysis revealed that the deposited film consisted of Cu, In and Se.

ALD of Compounds Comprising Selenide and Tellurium

Table 1 illustrates various thin films comprising tellurium or selenium that were deposited on glass and silicon substrates under various process conditions. The thin films in Table 1 were deposited using $Te(SiEt_3)_2$ as the tellurium source or $Se(SiEt_3)_2$ as the selenium source.

TABLE 1

| Material | Metal precursor/ evaporation temperature | Growth temperature | Growth rate by EDX (Å/cycle) | Composition by EDX | XRD |
|---|---|---|---|---|---|
| ZnTe | $ZnCl_2$/360° C. | 400° C. | 0.6 | Zn 47.0%, Te 53.0% | ZnTe |
| $Bi_2Te_3$ | $BiCl_3$/140° C. | 165° C. | 1.2 | Bi 39.7%, Te 60.3% | $Bi_2Te_3$ |
| ZnSe | $ZnCl_2$/360° C. | 400° C. | 0.55 | Zn 47.8%, Se 49.6%, Te 2.6%[1] | ZnSe |
| $Bi_2Se_3$ | $BiCl_3$/140° C. | 165° C. | 0.97 | Bi 41.1%, Se 58.9% | $Bi_2Se_3$ |
| $In_2Se_3$ | $InCl_3$/285° C. | 295° C. | 0.55 | In 40.6%, Se 59.4% | $In_2Se_3$ |
| CuSe | Cu(II)-pivalate/ 155° C. | 165° C. | 0.63 | Cu 50.1%, Se 49.9% | CuSe |
| $Cu_{2-x}Se$ | Cu(II)-pivalate/ 165° C. | 200° C. | 0.48 | Cu 61.5%, Se 38.5% | $Cu_{2-x}Se$ |
| $Cu_2Se$ | Cu(II)-pivalate/ 165° C. | 300° C. | 0.16 | Cu 69.2%, Se 30.8% | $Cu_2Se$ |
| $Cu_2Se$ | CuCl/350° C. | 400° C. | —[2] | —[2] | $Cu_2Se$ |

[1]Te contamination from previous runs
[2]no measurement

As shown in Table 1, the growth temperatures were higher for depositing some films because the metal precursors had higher evaporation temperatures. The results confirm that $Te(SiEt_3)_2$ and $Se(SiEt_3)_2$ precursors can be used at higher temperatures, for example at approximately 300° C.-400° C. In general, the thin films formed in Table 1 exhibited good growth rates. Further, the compositions for most of the thin films were close to the theoretical stoichiometric ratio.

In general, the deposited thin films appeared to be of good quality with little visible variation across the thin film surface.

The deposited copper-selenium (Cu—Se) thin films illustrated interesting results with Cu(II)-pivalate as the copper precursor. The stoichiometry of the deposited thin film varied with the growth temperature. CuSe was deposited at growth temperature of 165° C. $Cu_{2-x}Se$ was deposited at a growth temperature of 200° C. $Cu_2Se$ was deposited at a growth temperature of 300° C.

In some embodiments, any of the thin films described above can be doped with desired dopants for phase change memory applications, such as N, O, Si, S, In, Ag, Sn, Au, As, Bi, Zn, Se, Te, Ge, Sb and Mn, by adding pulses of a corresponding precursor to the growth process.

For example, for solar cells absorber materials like CuInSe$_2$ some of the In can be replaced, for example, by Ga and some of the Se can be replaced by, for example S, to modify the properties of the film to achieve the desired properties.

In some embodiments solar cell absorber materials can comprise Te. In some embodiments solar cell absorber materials can comprise Se.

In some embodiments Cu—Se thin films can be used as solar cell absorber materials. In other embodiments Cu—Se thin films can be modified to form solar cell absorber materials, for example, by doping as described above or other modification of the properties of the Cu—Se thin films. In some embodiments Cu—In—Se thin films can be used as solar cell absorber materials. In some embodiments, Cu—In—Se thin films doped to replace some or all of the In or Se atoms are used as solar cell absorber materials.

In some embodiments, any of the thin films described above can be deposited on any kind of substrate or surface such as, silicon, silicon oxide, silicon with native oxide, glass, semiconductor, metal oxide, and metal. In some cases, a metal surface, such as a tungsten surface, is preferred because of the higher growth rate as shown in FIG. 3. Other suitable metal surfaces include, but are not limited to, TiN, TaN$_x$, Ti, Ta, Nb, NbN$_x$, MoN$_x$, Mo, WN$_x$, Cu, Co, Ni, Fe, Al and noble metals.

Te(SiR$^1$R$^2$R$^3$)$_2$ or Se(SiR$^1$R$^2$R$^3$)$_2$ have suitable vapor pressures at relatively low temperatures and relatively high decomposition temperatures, which are required for ALD processes. Thus those precursors can be used for ALD of other films than those described in this application.

Precursor Synthesis

Methods are also provided for making some of the precursors used in the ALD processes described herein. In some embodiments, the precursor comprising Te or Se has a Te or Se atom bound to two silicon atoms. In particular, Te and Se precursors having a formula of Te(SiR$^1$R$^2$R$^3$)$_2$ or Se(SiR$^1$R$^2$R$^3$)$_2$, wherein R$^1$, R$^2$, and R$^3$ are preferably alkyl groups with one or more carbon atoms, can be synthesized. In some embodiments the Te precursor that is synthesized is Te(SiMe$_2$$^t$Bu)$_2$ and in other embodiments is Te(SiEt$_3$)$_2$. The Se precursor that is synthesized is Se(SiMe$_2$$^t$Bu)$_2$ in some embodiments and Se(SiEt$_3$)$_2$ in other embodiments.

In some embodiments the Te or Se precursor that is synthesized has a general formula of A(SiR$^1$R$^2$R$^3$)$_2$, wherein A is Te or Se and R$^1$, R$^2$, and R$^3$ are alkyl groups comprising one or more carbon atoms. The R$^1$, R$^2$, and R$^3$ alkyl groups can be selected independently of each other in each ligand based on the desired physical properties of the precursor such as volatility, vapor pressure, toxicity, etc. In some embodiments, R$^1$, R$^2$ and/or R$^3$ can be hydrogen, alkenyl, alkynyl or aryl groups. In some embodiments R$^1$, R$^2$, R$^3$ can be any organic groups containing heteroatoms, such as N, O, F, Si, P, S, Cl, Br or I. In some embodiments R$^1$, R$^2$, R$^3$ can be halogen atoms. In some embodiments the Te precursor is Te(SiMe$_2$$^t$Bu)$_2$ and the Se precursor is Se(SiMe$_2$$^t$Bu)$_2$. In other embodiments the precursor is Te(SiEt$_3$)$_2$, Te(SiMe$_3$)$_2$, Se(SiEt$_3$)$_2$ or Se(SiMe$_3$)$_2$. In more preferred embodiments the precursor has a Te—Si or Se—Si bond and most preferably Si—Te—Si or Si—Se—Si bond structure.

In some embodiments the Te or Se precursor that is synthesized has a Te or Se atom bound to two silicon atoms. For example, the precursor may have a general formula of [R$^1$R$^2$R$^3$X$^1$]$_3$—Si-A-Si—[X$^2$R$^4$R$^5$R$^6$]$_3$, wherein A is Te or Se; and wherein R$^1$, R$^2$, R$^3$, R$^4$, R$^5$ and R$^6$, can be independently selected to be alkyl, hydrogen, alkenyl, alkynyl or aryl groups. In some embodiments R$^1$, R$^2$, R$^3$, R$^4$, R$^5$ and R$^6$ can be any organic group containing heteroatoms, such as N, O, F, Si, P, S, Cl, Br or I. In some embodiments R$^1$, R$^2$, R$^3$, R$^4$, R$^5$ and R$^6$ can be halogen atoms. In some embodiments X$^1$ and X$^2$ can be Si, N, or O. In some embodiments X$^1$ and X$^2$ are different elements. In embodiments when X is Si then Si will be bound to three R groups, for example [R$^1$R$^2$R$^3$Si]$_3$—Si-A-Si—[SiR$^4$R$^5$R$^6$]$_3$. In embodiments when X is N then nitrogen will only be bound to two R groups ([R$^1$R$^2$N]$_3$—Si-A-Si—[NR$^3$R$^4$]$_3$). In embodiments when X is O, then oxygen will only be bound to one R group, for example [R$^1$—O]$_3$—Si-A-Si—[O—R$^2$]$_3$. R$^1$, R$^2$, R$^3$, R$^4$, R$^5$ and R$^6$ groups can be selected independently of each other in each ligand based on the desired physical properties of the precursor such as volatility, vapor pressure, toxicity, etc In some embodiments the Te or Se precursor that is synthesized has a formula similar to the formulas described above, however the Si atom has a double bond to one of the R groups in the ligand (e.g. A—Si=) wherein A is Te or Se. For example, a partial structure of the precursor formula is represented below:

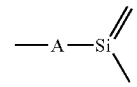

In some embodiments the precursor that is synthesized contains multiple atoms of Si and Te or Se. For example, a partial structure of a precursor in one embodiment is represented below wherein A is Te or Se:

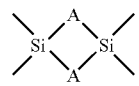

The Si atoms in the partial formula pictured above can also be bound to one or more R groups. In some embodiments, any of the R groups described herein can be used.

In some embodiments the precursor that is synthesized contains a Si—Te—Si or Si—Se—Si bond structure in a cyclical or ring structure. For example, a partial structure of a precursor in one embodiment is represented below, wherein A is Te or Se.

R group can comprise an alkyl, alkenyl, alkynyl, alkylsilyl, alkylamine or alkoxide group. In some embodiments the R group is substituted or branched. In some embodiments the R group is not substituted and/or is not branched. The Si atoms in the partial formula pictured above can also be bound to one or more R groups. In some embodiments, any of the R groups described herein can be used.

Figure 18:
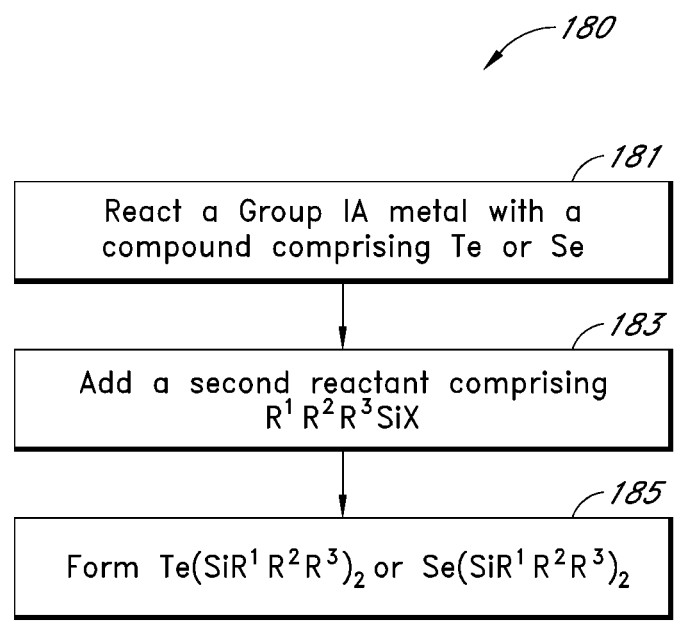
FIG. 18 is a flow chart generally illustrating a method for forming Te and Se precursors in accordance with one embodiment.

FIG. 18 is a flowchart generally illustrating methods for forming Te or Se precursors 180. In some embodiments the process for making a Te or Se precursor comprises:

forming a first product by reacting a Group IA metal with a material comprising Te or Se 181; and subsequently adding a second reactant comprising $R^1R^2R^3SiX$ to the first product, wherein $R^1$, $R^2$ and $R^3$ are alkyl groups with one or more carbon atoms and X is a halogen atom 183, thereby forming $A(SiR^1R^2R^3)_2$, wherein A is Te or Se 185.

In some embodiments, a Group IA elemental metal, such as Li, Na, K, etc. is combined with elemental Te or Se. In some embodiments the material comprising Te or Se is elemental Te or Se. Preferably, the Group IA element is provided as a powder or flakes and the elemental Te or Se is provided as a metal powder.

In some embodiments, a solvent, such as tetrahydrofuran (THF, $(CH_2)_4O$), is added to the Group IA metal and Te or Se. Preferably, naphthalene ($C_{10}H_8$) is added to the mixture to facilitate the solubility of IA metal and therefore also to help reduce Te or Se.

In some embodiments, the mixture is heated and a reflux condenser is used to reflux the solution under an inert gas such as Argon until completion of the reaction. During the reflux period, the color of the solution changes from clear and colorless to violet (with lithium as the reactant, other Group IA elements produce different colors) and then to a clear solution with a white precipitate. After a desired intermediate product is formed, the solution can be cooled down.

In some embodiments, a silicon containing compound is then added to the mixture. Preferably the silicon containing compound comprises a silicon atom bound to a halogen atom. Preferably, the silicon containing compound has a formula of $R^1R^2R^3SiX$, wherein $R^1$, $R^2$, and $R^3$ are preferably alkyl groups with one or more carbon atoms and X is preferably a halogen atom. $R^1$, $R^2$, and $R^3$ can be chosen based on the desired precursor properties of the final product, including vapor pressure, melting point, etc. In some embodiments, $R^1$, $R^2$ and/or $R^3$ can be hydrogen, alkenyl, alkynyl or aryl groups. In some embodiments, $R^1$, $R^2$, $R^3$ can be any organic group containing heteroatoms, such as N, O, F, Si, P, S, Cl, Br or I. In some embodiments $R^1$, $R^2$, $R^3$ can be halogen atoms. In some embodiments $R^1$, $R^2$, and $R^3$ can all be the same group. In other embodiments, $R^1$, $R^2$, and $R^3$ can all be different groups. In some embodiments, $R^1$, $R^2$, and $R^3$ are all ethyl groups ($Et_3$). In other embodiments $R^1$ and $R^2$ are methyl groups and $R^3$ is a tertbutyl group ($Me_2{}^tBu$). In some embodiments, X is Cl. In some preferred embodiments, the silicon containing compound has a formula of $Et_3SiCl$ or $^tBuMe_2SiCl$.

In some embodiments the silicon containing compound has a general formula of $[R^1R^2R^3X^1]_3$—Si—X, wherein $R^1$, $R^2$ and $R^3$, can be independently selected to be alkyl, hydrogen, alkenyl, alkynyl or aryl groups and X is preferably a halogen atom. In some embodiments $R^1$, $R^2$ and $R^3$ can be any organic group containing heteroatoms, such as N, O, F, Si, P, S, Cl, Br or I. In some embodiments $R^1$, $R^2$ and $R^3$ can be halogen atoms. In some embodiments $X^1$ can be Si, N, or O. In embodiments when $X^1$ is Si then Si will be bound to three R groups, for example $[R^1R^2R^3Si]_3$—Si—X. In embodiments when $X^1$ is N then nitrogen will only be bound to two R groups ($[R^1R^2N]_3$—Si—X. In embodiments when $X^1$ is O, then oxygen will only be bound to one R group, for example $[R^1$—$O]_3$—Si—X. $R^1$, $R^2$ and $R^3$ groups can be selected independently of each other in each ligand based on the desired physical properties of the precursor such as volatility, vapor pressure, toxicity, etc In some embodiments the silicon containing compound has a formula similar to the formulas described above, however the Si atom has a double bond to one of the R groups in the ligand (e.g. bond structure X—Si=R) wherein R can be independently selected to be alkyl, hydrogen, alkenyl, alkynyl or aryl groups and X is preferably a halogen atom. In some embodiments, R can be any organic group containing heteroatoms such as N, O, F, Si, P, S, Cl, Br or I. For example, a partial structure of the silicon containing compound formula is represented below:

In some embodiments the silicon containing compound has a formula similar to the formulas described above, however the Si atom has two X atoms attached to silicon (e.g. bond structure $X_2$—Si—$R^1R^2$) wherein $R^1$ and $R^2$ can be independently selected to be alkyl, hydrogen, alkenyl, alkynyl or aryl groups and X is preferably a halogen atom. In some embodiments $R^1$ and $R^2$ can be any organic group containing heteroatoms such as N, O, F, Si, P, S, Cl, Br or I. For example, a partial structure of the silicon containing compound formula is represented below:

In some embodiments the silicon containing compound has a formula similar to the formulas described above, however there are two Si atoms bridged via R group (e.g. bond structure X—Si—R—Si—X) wherein R group can comprise an alkyl, alkenyl, alkynyl, alkylsilyl, alkylamine or alkoxide group. In some embodiments the R group is substituted or branched. In some embodiments the R group is not substituted and/or is not branched and X is preferably a halogen atom. In some embodiments, R can be any organic group containing heteroatoms such as N, O, F, Si, P, S, Cl, Br or I.

In some embodiments the silicon containing compound is selected from the group consisting of: $R^1R^2R^3Si$—Si—X, $R^1R^2N$—Si—X, $R^1$—O—Si—X, $R^1R^2Si$—X with a double bond between silicon and one of the R groups, or comprises $R^1R^2$—Si—$X_2$; wherein $R^1$, $R^2$, and $R^3$, are selected from the group consisting of alkyl, hydrogen, alkenyl, alkynyl, or aryl groups and X is a halogen atom. In some embodiments the silicon containing compound is not a compound of the formula $XSiR^1R^2R^3$.

The mixture is continuously stirred until the reaction is complete. After the reaction is substantially complete, the final product is separated and isolated from any solvents, by-products, excess reactants, or any other compounds that are not desired in the final product. The product can be a solid or liquid at standard temperature and pressure.

The following are examples of synthesizing Te compounds, but similar synthesis methods can be used to synthesize corresponding Se compounds.

Example 14

$Te(SiMe_2{}^tBu)_2$ was produced by the following process. First, 1.15 g of lithium (165.68 mmol) was added to 300 ml of dry THF along with 10.58 g (89.22 mmol) of Te powder and 0.7 g (5.47 mmol) of naphthalene in a 600 ml Schlenk bottle. The resultant mixture was heated and a reflux condenser was mounted on the bottle. The solution was refluxed with an argon atmosphere for about four hours. The solution was initially colorless with undissolved solid Li and Te. During, the reflux period the mixture turned a violet color and then back to a clear solution with a white precipitate. After the white precipitate was formed, the solution was cooled to 0° C.

Next, 25.00 g of $^t$BuMe$_2$SiCl (165.87 mmol) was added to the mixture. The mixture was constantly stirred at room temperature over night. The mixture was then evaporated to dryness. 100 ml of toluene was added to the dry mixture to facilitate filtering of the mixture. The toluene solution was then filtered. The filtrate, including the product, was then evaporated to dryness and heated under vacuum to remove any residual naphthalene contained in the crude product. The recovered product weighed 27.34 g resulting in a calculated reaction efficiency of about 77%. The composition of the product was verified to be Te(SiMe$_2$$^t$Bu)$_2$ by nuclear magnetic resonance (NMR), mass spectroscopy (MS) and single crystal x-ray diffraction. The Te(SiMe$_2$$^t$Bu)$_2$ produced was a solid with a melting point of 44° C.

Example 15

Te(SiEt$_3$)$_2$ was produced by a process similar to that described in Example 14. First, 0.23 g of lithium was added to 300 ml of dry THF along with 2.12 g of Te powder and 0.3 g of naphthalene in a 600 ml Schlenk bottle. The resultant mixture was heated and a reflux condenser was mounted on the bottle. The solution was refluxed with an argon atmosphere. Solution was initially colorless with undissolved solid Li and Te. During, the reflux period the mixture turned a violet color and then back to a clear solution with a white precipitate. After the white precipitate was formed, the solution was cooled to 0° C.

Next, 5.0 g of Et$_3$SiCl was added to the mixture. The mixture was constantly stirred at room temperature over night. The final product was isolated from the other reactants and any by-products. The recovered product weighed 4.8 g resulting in a reaction efficiency of about 80%. The composition of the product was verified to be Te(SiEt$_3$)$_2$ by nuclear magnetic resonance (NMk) and mass spectroscopy (MS). The compound was a brownish liquid at room temperature.

It will be appreciated by those skilled in the art that various modifications and changes can be made without departing from the scope of the invention. Similar other modifications and changes are intended to fall within the scope of the invention, as defined by the appended claims.

We claim:

1. An atomic layer deposition (ALD) process for forming a Te and/or Se containing thin film on a substrate in a reaction chamber comprising a plurality of deposition cycles, each cycle comprising:
   providing a pulse of a first vapor phase reactant into the reaction chamber to form no more than about a single molecular layer of the first reactant on the substrate, wherein the first reactant comprises a metal halide;
   removing excess first reactant from the reaction chamber;
   providing a pulse of a second vapor phase reactant to the reaction chamber such that the second reactant reacts with the first reactant on the substrate to form Te or Se containing compound thin film, wherein the second reactant is Te(SiR$^1$R$^2$R$^3$)$_2$ or Se(SiR$^1$R$^2$R$^3$)$_2$, wherein R$^1$, R$^2$, and R$^3$ are alkyl groups with one or more carbon atoms; and
   removing excess second reactant and reaction byproducts, if any, from the reaction chamber,
   wherein no reactants other than metal halides, Te(SiR$^1$R$^2$R$^3$)$_2$ and Se(SiR$^1$R$^2$R$^3$)$_2$ are provided in the deposition process.

2. The method of claim 1, wherein the Te or Se in the second reactant is not bound to a hydrogen atom.

3. The method of claim 1, wherein the Te or Se in the second reactant has an oxidation state of −2.

4. The method of claim 1, wherein the second reactant is Te(SiEt$_3$)$_2$, Te(SiMe$_3$)$_2$, Se(SiEt$_3$)$_2$, or Se(SiMe$_3$)$_2$.

5. The method of claim 1, wherein the first reactant comprises Sb, wherein the second reactant comprises Te.

6. The process of claim 5, wherein the deposition temperature is less than about 80° C.

7. The method of claim 5, wherein the first reactant is SbCl$_3$.

8. The method of claim 5, further comprising multiple Ge—Te deposition cycles, wherein the Ge—Te deposition cycles comprise:
   providing a third vapor phase reactant pulse comprising a Ge precursor into the reaction chamber to form no more than about a single molecular layer of the Ge precursor on the substrate;
   removing excess first reactant from the reaction chamber;
   providing a fourth vapor phase reactant pulse comprising a Te precursor to the reaction chamber such that the Te precursor reacts with the Ge precursor on the substrate, wherein the Te precursor has the formula Te(SiR$^1$R$^2$R$^3$)$_2$, wherein R$^1$, R$^2$, and R$^3$ are alkyl groups.

9. The method of claim 8, wherein the Ge—Te deposition cycles and Sb—Te deposition cycles are performed in about a 1:1 ratio.

10. The method of claim 8, wherein the Ge precursor comprises GeX$_2$, wherein X is a halogen.

11. The method of claim 8, wherein the second reactant and fourth precursor are each either Te(SiEt$_3$)$_2$ or Te(SiMe$_3$)$_2$.

12. The method of claim 11, wherein the first reactant is SbCl$_3$.

13. The method of claim 12, wherein the third reactant comprises GeX$_2$, wherein X is a halogen.

14. The method of claim 1, wherein the first reactant pulse comprises Ge, wherein the deposited compound thin film comprises Ge—Te.

15. The method of claim 14, wherein the first reactant is GeBr$_2$.

16. The method of claim 1, wherein the first reactant comprises Bi, wherein the deposited film comprises Bi—Te.

17. The method of claim 16, wherein the first reactant is BiX$_3$, wherein X is a halogen.

18. The method of claim 16, wherein the first reactant is BiCl$_3$.

19. The method of claim 1, wherein the first reactant comprises Zn, wherein the deposited film comprises Zn—Te.

20. The method of claim 19, wherein the first reactant is ZnX$_2$, wherein X is a halogen.

21. The method of claim 19, wherein the first reactant is ZnCl$_2$.

22. The method of claim 1, wherein the compound film comprises phase change memory.

23. The method of claim 1, wherein the compound film comprises one or more of Sb—Te, Ge—Te, Ge—Sb—Te, Bi—Te, or Zn—Te.

24. The method of claim 1, wherein the compound film comprises Ge—Sb—Te.

25. The method of claim 1, wherein the compound thin film comprises one or more of Sb—Te, Ge—Te, Ge—Sb—Te, Bi—Te, or Zn—Te doped with one or more dopants comprising O, N, Si, S, In, Ag, Sn, Au, As, Bi, Zn, Se, Te, Ge, Sb, and Mn.

26. The method of claim 1, wherein the compound film comprises a solar cell absorber.

27. The method of claim 1, wherein the first reactant comprises Bi, wherein the deposited film comprises Bi—Se.

28. The method of claim 27, wherein the first reactant is $BiX_3$, wherein X is a halogen.

29. The method of claim 27, wherein the second reactant is $Se(SiEt_3)_2$.

30. The method of claim 1, wherein the first reactant comprises Cu, wherein the deposited film comprises Cu—Se.

31. The method of claim 30, wherein the second reactant is $Se(SiEt_3)_2$.

32. The method of claim 30, wherein the first reactant is CuCl.

33. The method of claim 30, further comprising multiple In—Se deposition cycles, wherein the In—Se deposition cycles comprise:
   providing a third vapor phase reactant pulse comprising an In precursor into the reaction chamber to form no more than about a single molecular layer of the In precursor on the substrate;
   removing excess third reactant from the reaction chamber;
   providing a fourth vapor phase reactant pulse comprising an Se precursor to the reaction chamber such that the Se precursor reacts with the In precursor on the substrate, wherein the Se precursor has the formula $Se(SiR^1R^2R^3)_2$, wherein $R^1$, $R^2$, and $R^3$ are alkyl groups.

34. The method of claim 33, wherein the In—Se deposition cycles and Cu—Se deposition cycles are performed in about a 1:1 ratio.

35. The method of claim 33, wherein the In precursor is $InX_3$, wherein X is a halogen and the Se precursor is $Se(SiEt_3)_2$.

36. The method of claim 1, wherein each deposition cycle deposits greater than about 0.1 Å of the Te or Se containing thin film.

37. The method of claim 1, wherein the metal halide comprises a germanium halide.

38. An atomic layer deposition (ALD) method for forming a Te or Se containing thin film comprising:
   alternately and sequentially contacting a substrate with a vapor phase reactant pulse comprising a first reactant and a vapor phase reactant pulse comprising a second precursor comprising Te or Se, wherein the first reactant comprises a metal halide, wherein the second precursor is $Te(SiR^1R^2R^3)_2$ or $Se(SiR^1R^2R^3)_2$, wherein $R^1$, $R^2$, and $R^3$ are alkyl groups with one or more carbon atoms, and wherein a different reactant is not provided while alternately and sequentially contacting the substrate with the vapor phase reactant pulse comprising the first reactant and the vapor phase reactant pulse comprising the second reactant; and
   repeating the alternate and sequential pulses until a compound thin film of a desired thickness is obtained.

39. The method of claim 38, wherein the Te or Se in the second precursor has an oxidation state of −2.

40. The method of claim 38, wherein the Te or Se in the second precursor is not bound to a hydrogen atom.

41. The method of claim 38, wherein alternate and sequential pulses of the first reactant and second precursor comprising Te or Se comprises a deposition cycle, wherein each deposition cycle deposits greater than about 0.1 Å of the Te or Se containing thin film.

42. The method of claim 38, wherein the metal halide comprises a germanium halide.

* * * * *

UNITED STATES PATENT AND TRADEMARK OFFICE
CERTIFICATE OF CORRECTION

PATENT NO.       : 9,175,390 B2
APPLICATION NO.  : 12/429133
DATED            : November 3, 2015
INVENTOR(S)      : Viljami Pore et al.

It is certified that error appears in the above-identified patent and that said Letters Patent is hereby corrected as shown below:

On the title page

In column 1 (page 2, item 56) at line 50, Under Other Publications, change ""Room-Termperature" to --"Room-Temperature--.

In column 2 (page 2, item 56) at line 12, Under Other Publications, change "Ligan" to --Ligand--.

In column 2 (page 2, item 56) at line 15, Under Other Publications, change "Organotin-nitroen" to --Organotin-nitrogen--.

In column 2 (page 2, item 56) at line 17, Under Other Publications, change "trirnethylsily" to --trimethylsilyl--.

In column 2 (page 2, item 56) at lines 38-39, Under Other Publications, change "adamantine" to --adamantane--.

In the specification

In column 3 at line 47, Change "susbstrate" to --substrate--.

In column 7 at line 30, After "etc" insert --.--.

In column 8 at line 37, Change "Hg," to --Hg.--.

In column 22 at line 20 (approx.), After "etc" insert --.--.

In column 23 at line 64, After "etc" insert --.--.

In column 25 at line 41, Change "(NMk)" to --(NMR)--.

In the claims

In column 26 at line 12 (approx.), In claim 6, change "The process of" to --The method of--.

Signed and Sealed this
Nineteenth Day of July, 2016

Michelle K. Lee
*Director of the United States Patent and Trademark Office*